US008882980B2

(12) United States Patent
Ling et al.

(10) Patent No.: US 8,882,980 B2
(45) Date of Patent: *Nov. 11, 2014

(54) USE OF LONGITUDINALLY DISPLACED NANOSCALE ELECTRODES FOR VOLTAGE SENSING OF BIOMOLECULES AND OTHER ANALYTES IN FLUIDIC CHANNELS

(75) Inventors: Xinsheng Ling, East Greenwich, RI (US); Barrett Bready, Providence, RI (US); John S. Oliver, Bristol, RI (US); Maryam Jouzi, Cambridge, MA (US); Leo Petrossian, Providence, RI (US)

(73) Assignee: NABsys, Inc., Providence, RI (US)

( * ) Notice: Subject to any disclaimer, the term of this patent is extended or adjusted under 35 U.S.C. 154(b) by 261 days.

This patent is subject to a terminal disclaimer.

(21) Appl. No.: 12/553,667

(22) Filed: Sep. 3, 2009

(65) Prior Publication Data
US 2010/0096268 A1    Apr. 22, 2010

Related U.S. Application Data

(60) Provisional application No. 61/093,885, filed on Sep. 3, 2008.

(51) Int. Cl.
| | | |
|---|---|---|
| *G01N 27/447* | (2006.01) | |
| *G01N 27/26* | (2006.01) | |
| *G01N 33/487* | (2006.01) | |
| *B82Y 15/00* | (2011.01) | |
| *C07K 1/26* | (2006.01) | |
| *B01L 3/00* | (2006.01) | |
| *G01N 27/327* | (2006.01) | |

(52) U.S. Cl.
CPC .......... *G01N 33/48721* (2013.01); *B82Y 15/00* (2013.01); *B01L 3/502761* (2013.01); *G01N 27/3278* (2013.01); *Y10S 977/957* (2013.01)
USPC .......................... 204/452; 204/603; 977/957

(58) Field of Classification Search
USPC ............. 204/192.22, 433, 450; 205/549, 645; 422/500–570
See application file for complete search history.

(56) References Cited

U.S. PATENT DOCUMENTS 3,699,437 A    10/1972  Ur
H201 H         1/1987   Yager
(Continued)

FOREIGN PATENT DOCUMENTS

DE    19936302       2/2001
EP    0958495 A1     11/1999
(Continued)

OTHER PUBLICATIONS

Liang et al. Nano Letters vol. 8 No. 5 pp. 1472-1476 (Apr. 17, 2008).*
(Continued)

*Primary Examiner* — Luan Van
*Assistant Examiner* — Steven Rosenwald
(74) *Attorney, Agent, or Firm* — Goodwin Procter LLP

(57) ABSTRACT

Devices and methods for detecting an analyte are provided. Devices for voltage sensing of analytes may comprise a fluidic channel defined in a substrate, a pair of sensing electrodes disposed in a fluidic channel for sensing voltage therein, and a pair of electromotive electrodes for applying potential along the fluidic channel. The pair of sensing electrodes may include a first and second sensing electrode disposed at two discrete locations along the length of the fluidic channel and the pair of electromotive electrodes may be disposed at a first end and a second end of the fluidic channel. The fluidic channel may include a nanochannel or a microchannel. Methods for detecting an analyte may include the steps of disposing the analyte in a fluidic channel; applying a potential along the fluidic channel to generate an electrophoretic force therein such that the analyte is translocated from a first end of the fluidic channel to a second end of the fluidic channel; and measuring a voltage signal between a pair of sensing electrodes disposed in the fluidic channel as the analyte moves past the sensing electrodes.

56 Claims, 9 Drawing Sheets

(56) References Cited

U.S. PATENT DOCUMENTS

| | | |
|---|---|---|
| 4,810,650 A | 3/1989 | Kell et al. |
| 4,874,499 A | 10/1989 | Smith et al. |
| 5,194,133 A | 3/1993 | Clark et al. |
| 5,202,231 A | 4/1993 | Drmanac et al. |
| 5,246,552 A * | 9/1993 | Kamiya et al. ............. 205/701 |
| 5,314,829 A | 5/1994 | Coles |
| 5,405,519 A | 4/1995 | Schwartz |
| 5,427,663 A | 6/1995 | Austin et al. |
| 5,455,166 A | 10/1995 | Walker |
| 5,539,082 A | 7/1996 | Nielsen et al. |
| 5,560,811 A | 10/1996 | Briggs et al. |
| 5,599,664 A | 2/1997 | Schwartz |
| 5,650,305 A | 7/1997 | Hui et al. |
| 5,681,947 A | 10/1997 | Bergstrom et al. |
| 5,683,881 A | 11/1997 | Skiena |
| 5,720,928 A | 2/1998 | Schwartz |
| 5,744,366 A | 4/1998 | Kricka et al. |
| 5,773,571 A | 6/1998 | Nielsen et al. |
| 5,795,782 A | 8/1998 | Church et al. |
| 5,824,477 A | 10/1998 | Stanley |
| 5,837,115 A | 11/1998 | Austin et al. |
| 5,908,745 A | 6/1999 | Mirzabekov et al. |
| 5,972,619 A | 10/1999 | Drmanac et al. |
| 6,015,714 A | 1/2000 | Baldarelli et al. |
| 6,020,599 A | 2/2000 | Yeo |
| 6,025,891 A | 2/2000 | Kim |
| 6,084,648 A | 7/2000 | Yeo |
| 6,100,949 A | 8/2000 | Kim |
| 6,108,666 A | 8/2000 | Floratos et al. |
| 6,128,051 A | 10/2000 | Kim et al. |
| 6,147,198 A | 11/2000 | Schwartz |
| 6,150,089 A | 11/2000 | Schwartz |
| 6,174,671 B1 | 1/2001 | Anantharaman et al. |
| 6,182,733 B1 | 2/2001 | McReynolds |
| 6,210,891 B1 | 4/2001 | Nyren et al. |
| 6,210,896 B1 | 4/2001 | Chan |
| 6,258,568 B1 | 7/2001 | Nyren |
| 6,263,286 B1 | 7/2001 | Gilmanshin et al. |
| 6,267,872 B1 | 7/2001 | Akeson et al. |
| 6,274,320 B1 | 8/2001 | Rothberg et al. |
| 6,294,136 B1 | 9/2001 | Schwartz |
| 6,303,288 B1 * | 10/2001 | Furcht et al. ............. 435/4 |
| 6,304,318 B1 | 10/2001 | Matsumoto |
| 6,340,567 B1 | 1/2002 | Schwartz et al. |
| 6,355,420 B1 | 3/2002 | Chan |
| 6,362,002 B1 | 3/2002 | Denison et al. |
| 6,392,719 B2 | 5/2002 | Kim |
| 6,400,425 B1 | 6/2002 | Kim et al. |
| 6,403,311 B1 | 6/2002 | Chan |
| 6,410,243 B1 | 6/2002 | Wyrick et al. |
| 6,413,792 B1 | 7/2002 | Sauer et al. |
| 6,428,959 B1 | 8/2002 | Deamer |
| 6,448,012 B1 | 9/2002 | Schwartz |
| 6,464,842 B1 * | 10/2002 | Golovchenko et al. .. 204/192.13 |
| 6,503,409 B1 | 1/2003 | Fleming |
| 6,509,158 B1 | 1/2003 | Schwartz |
| 6,537,755 B1 | 3/2003 | Drmanac |
| 6,537,765 B2 | 3/2003 | Stricker-Kongra et al. |
| 6,610,256 B2 | 8/2003 | Schwartz |
| 6,617,113 B2 | 9/2003 | Deamer |
| 6,627,067 B1 * | 9/2003 | Branton et al. ............. 205/778 |
| 6,672,067 B2 | 1/2004 | Farmer et al. |
| 6,673,615 B2 | 1/2004 | Denison et al. |
| 6,685,841 B2 | 2/2004 | Lopez et al. |
| 6,689,563 B2 | 2/2004 | Preparata et al. |
| 6,696,022 B1 | 2/2004 | Chan et al. |
| 6,713,263 B2 | 3/2004 | Schwartz |
| 6,746,594 B2 | 6/2004 | Akeson et al. |
| 6,762,059 B2 | 7/2004 | Chan et al. |
| 6,772,070 B2 | 8/2004 | Gilmanshin et al. |
| 6,790,671 B1 | 9/2004 | Austin et al. |
| 6,818,395 B1 | 11/2004 | Quake et al. |
| 6,905,586 B2 | 6/2005 | Lee et al. |
| 6,911,345 B2 | 6/2005 | Quake et al. |
| 6,919,002 B2 | 7/2005 | Chopra |
| 6,927,065 B2 | 8/2005 | Chan et al. |
| 6,936,433 B2 | 8/2005 | Akeson et al. |
| 7,001,792 B2 | 2/2006 | Sauer et al. |
| 7,005,264 B2 | 2/2006 | Su et al. |
| 7,034,143 B1 | 4/2006 | Preparata et al. |
| 7,071,324 B2 | 7/2006 | Preparata et al. |
| 7,118,657 B2 | 10/2006 | Golovchenko et al. |
| 7,170,050 B2 | 1/2007 | Turner et al. |
| 7,176,007 B2 | 2/2007 | Cox et al. |
| 7,189,503 B2 | 3/2007 | Akeson et al. |
| 7,211,414 B2 | 5/2007 | Hardin et al. |
| 7,217,562 B2 | 5/2007 | Cao et al. |
| 7,238,485 B2 | 7/2007 | Akeson et al. |
| 7,248,771 B2 | 7/2007 | Schmidt et al. |
| 7,250,115 B2 | 7/2007 | Barth |
| 7,262,859 B2 | 8/2007 | Larson et al. |
| 7,279,337 B2 | 10/2007 | Zhu |
| 7,282,130 B2 | 10/2007 | Flory |
| 7,282,330 B2 | 10/2007 | Zhao et al. |
| 7,297,518 B2 | 11/2007 | Quake et al. |
| 7,302,146 B2 | 11/2007 | Turner et al. |
| 7,315,019 B2 | 1/2008 | Turner et al. |
| 7,329,492 B2 | 2/2008 | Hardin et al. |
| 7,351,538 B2 | 4/2008 | Fuchs et al. |
| 7,355,216 B2 | 4/2008 | Yang et al. |
| 7,371,520 B2 | 5/2008 | Zhao et al. |
| 7,402,422 B2 | 7/2008 | Fuchs et al. |
| 7,462,449 B2 | 12/2008 | Quake |
| 7,476,503 B2 | 1/2009 | Turner et al. |
| 7,476,504 B2 | 1/2009 | Turner |
| 7,501,245 B2 | 3/2009 | Quake et al. |
| 7,595,160 B2 | 9/2009 | White et al. |
| 7,678,562 B2 | 3/2010 | Ling |
| 8,232,055 B2 | 7/2012 | Bruhn et al. |
| 8,278,050 B2 | 10/2012 | Bailey et al. |
| 8,333,934 B2 | 12/2012 | Cao et al. |
| 8,455,260 B2 | 6/2013 | Goldstein et al. |
| 8,628,919 B2 | 1/2014 | Xiao et al. |
| 8,715,933 B2 | 5/2014 | Oliver |
| 2001/0004728 A1 | 6/2001 | Preparata et al. |
| 2002/0025277 A1 * | 2/2002 | Dugas et al. ............. 422/88 |
| 2002/0028458 A1 | 3/2002 | Lexow |
| 2002/0058279 A1 | 5/2002 | Fritsch et al. |
| 2002/0127855 A1 | 9/2002 | Sauer et al. |
| 2002/0137089 A1 | 9/2002 | Deamer |
| 2002/0150961 A1 | 10/2002 | Bogyo et al. |
| 2003/0003609 A1 | 1/2003 | Sauer et al. |
| 2003/0064095 A1 | 4/2003 | Martin et al. |
| 2003/0064382 A1 | 4/2003 | Preparata et al. |
| 2003/0080042 A1 | 5/2003 | Barth et al. |
| 2003/0104428 A1 | 6/2003 | Branton et al. |
| 2003/0143614 A1 | 7/2003 | Drmanac |
| 2003/0186256 A1 | 10/2003 | Fischer |
| 2003/0207326 A1 | 11/2003 | Su et al. |
| 2003/0211502 A1 | 11/2003 | Sauer et al. |
| 2003/0232346 A1 | 12/2003 | Su |
| 2004/0137734 A1 | 7/2004 | Chou et al. |
| 2004/0146430 A1 | 7/2004 | Dugas |
| 2004/0197843 A1 | 10/2004 | Chou et al. |
| 2005/0019784 A1 | 1/2005 | Su et al. |
| 2005/0127035 A1 | 6/2005 | Ling |
| 2005/0202444 A1 * | 9/2005 | Zhu ................ 435/6 |
| 2006/0019247 A1 | 1/2006 | Su et al. |
| 2006/0063171 A1 | 3/2006 | Akeson et al. |
| 2006/0154399 A1 | 7/2006 | Sauer et al. |
| 2006/0269483 A1 | 11/2006 | Austin et al. |
| 2006/0287833 A1 | 12/2006 | Yakhini |
| 2007/0020772 A1 | 1/2007 | Cao et al. |
| 2007/0039920 A1 | 2/2007 | Kutchoukov et al. |
| 2007/0042366 A1 | 2/2007 | Ling |
| 2007/0080511 A1 | 4/2007 | Campbell |
| 2007/0084163 A1 | 4/2007 | Lai |
| 2007/0084702 A1 | 4/2007 | Lin et al. |
| 2007/0138132 A1 | 6/2007 | Barth |
| 2007/0178240 A1 | 8/2007 | Yamazaki et al. |
| 2007/0190542 A1 | 8/2007 | Ling et al. |
| 2007/0218471 A1 | 9/2007 | Kim et al. |
| 2007/0231795 A1 | 10/2007 | Su |
| 2007/0238112 A1 | 10/2007 | Sohn et al. |

(56) References Cited

U.S. PATENT DOCUMENTS

| | | | |
|---|---|---|---|
| 2008/0041733 A1 | 2/2008 | Hibbs et al. | |
| 2008/0085840 A1 | 4/2008 | Buzby | |
| 2008/0096287 A1 | 4/2008 | Barth | |
| 2008/0102504 A1 | 5/2008 | Akeson et al. | |
| 2008/0119366 A1 | 5/2008 | Sauer et al. | |
| 2008/0171316 A1 | 7/2008 | Golovchenko et al. | |
| 2008/0187915 A1 | 8/2008 | Polonsky et al. | |
| 2008/0234136 A1 | 9/2008 | Drmanac et al. | |
| 2008/0242556 A1 | 10/2008 | Cao et al. | |
| 2008/0254995 A1* | 10/2008 | Kim et al. | 506/4 |
| 2009/0005252 A1 | 1/2009 | Drmanac et al. | |
| 2009/0011943 A1 | 1/2009 | Drmanac et al. | |
| 2009/0035777 A1 | 2/2009 | Kokoris et al. | |
| 2009/0099786 A1 | 4/2009 | Oliver et al. | |
| 2009/0111115 A1 | 4/2009 | Drmanac et al. | |
| 2009/0117540 A1 | 5/2009 | Sorge | |
| 2009/0136948 A1 | 5/2009 | Han et al. | |
| 2009/0176652 A1 | 7/2009 | Dahl et al. | |
| 2009/0214392 A1 | 8/2009 | Kameoka et al. | |
| 2010/0078325 A1 | 4/2010 | Oliver | |
| 2010/0096268 A1 | 4/2010 | Ling et al. | |
| 2010/0143960 A1 | 6/2010 | Bazin | |
| 2010/0243449 A1 | 9/2010 | Oliver | |
| 2010/0297644 A1 | 11/2010 | Kokoris et al. | |
| 2010/0310421 A1 | 12/2010 | Oliver et al. | |
| 2012/0074925 A1 | 3/2012 | Oliver | |
| 2012/0208193 A1 | 8/2012 | Okino et al. | |
| 2013/0011934 A1 | 1/2013 | Oliver et al. | |
| 2014/0087390 A1 | 3/2014 | Oliver et al. | |

FOREIGN PATENT DOCUMENTS

| | | |
|---|---|---|
| EP | 1486775 | 12/2004 |
| EP | 1685407 | 8/2006 |
| JP | 2002526759 A | 8/2002 |
| JP | 2003-028826 A | 1/2003 |
| JP | 2003510034 A | 3/2003 |
| JP | 2003513279 A | 4/2003 |
| JP | 2004004064 A | 1/2004 |
| JP | 2007068413 A | 3/2007 |
| WO | WO-9004652 | 5/1990 |
| WO | WO-9322678 A2 | 11/1993 |
| WO | WO-9617957 | 6/1996 |
| WO | WO-9835012 | 8/1998 |
| WO | WO-0009757 | 2/2000 |
| WO | WO-0011220 A1 | 3/2000 |
| WO | WO-0020626 A1 | 4/2000 |
| WO | WO-0022171 | 4/2000 |
| WO | WO-0062931 A1 | 10/2000 |
| WO | WO 01/18246 A1 * | 3/2001 |
| WO | WO-0118246 | 3/2001 |
| WO | WO-0131063 A1 | 5/2001 |
| WO | WO-0133216 A1 | 5/2001 |
| WO | WO-0137958 | 5/2001 |
| WO | WO-0142782 | 6/2001 |
| WO | WO-0146467 A2 | 6/2001 |
| WO | WO-0207199 | 1/2002 |
| WO | WO-0250534 | 6/2002 |
| WO | WO-03000920 | 1/2003 |
| WO | WO-03010289 | 2/2003 |
| WO | WO-03079416 | 9/2003 |
| WO | WO-03089666 A2 | 10/2003 |
| WO | WO-03106693 | 12/2003 |
| WO | WO-2004035211 | 4/2004 |
| WO | WO-2004085609 | 10/2004 |
| WO | WO-2005017025 | 2/2005 |
| WO | WO-2006020775 | 2/2006 |
| WO | WO-2006028508 | 3/2006 |
| WO | WO-2006052882 | 5/2006 |
| WO | WO-2007041621 | 4/2007 |
| WO | WO-2007084076 A1 | 7/2007 |
| WO | WO-2007106509 | 9/2007 |
| WO | WO-2007111924 | 10/2007 |
| WO | WO-2007127327 | 11/2007 |
| WO | WO-2008021488 | 2/2008 |
| WO | WO-2008039579 | 4/2008 |
| WO | WO-2008042018 | 4/2008 |
| WO | WO-2008046923 | 4/2008 |
| WO | WO-2008049021 | 4/2008 |
| WO | WO-2008069973 | 6/2008 |
| WO | WO-2008079169 | 7/2008 |
| WO | WO-2009046094 | 4/2009 |
| WO | WO-2010002883 A2 | 1/2010 |
| WO | WO-2010111605 | 9/2010 |
| WO | WO-2010138136 | 12/2010 |
| WO | WO-2011109825 A2 | 9/2011 |
| WO | WO-2012109574 A2 | 8/2012 |
| WO | WO-2014052433 A2 | 4/2014 |

OTHER PUBLICATIONS

Wu et aL (Electrophoresis 2007, 28,4612-4619).*
Akeson, et al., "Microsecond time-scale discrimination among polycytidylic acid, polyadenylic acid, and polyuridylic acid as homopolymers or as segments within single RNA molecules," Biophys. J. 77, 3227-3233 (1999).
Ashkin, "Optical trapping and manipulation of neutral particles using lasers," Proc. Natl. Acad. Sci. USA, vol. 94, DD. 4853-4860, May 1997.
International Search Report for PCT/US04/04138, dated May 4, 2006, 5 pages.
International Search Report and Written Opinion for PCT/US09/558876 dated Feb. 10, 2010, 5 pages.
Partial International Search Report for PCT/US09/055878 dated Feb. 15, 2010, 3 pages.
Kuo, et al., "Hybrid three-dimensional nanofluidic/microfluidic devices using molecular gates," Sensors and Actuators A, vol. 102 (Oct. 2002):223-233.
Langa, "Self-organized growth of single crystals of nanopores," Applied Physics Letters, AIP, American Institute of Physics, 2003, vol. 82, No. 2, pp. 278-280.
Li et al., "Ion-beam sculpting at nanometre length scales", Nature 412,166-169 (2001).
Losi, et al., "Time-Resolved Absorption and Photothermal Measurements with Recombinant Sensory Rhodopsin II from Natronobacterium pharaonis," Biophys. J. 77, 3277-3286, Dec. 1999.
Meller, et al., "Voltage-driven DNA translocations through a nanopore," Phys. Rev. Lett. 86(15),3435-3438 (2001).
Storm, et al., "Fabrication of solid-state nanopores with single-nanometre precision," Nature Materials 2,537-540, Aug. 2003.
Alberts, B., et al., (1970) "T4 Bacteriophage Gene 32: A Structural Protein in the Replication and Recombination of DNA," Nature 227:1313-1318.
Amit, B., et al., (1974) "Photosensitive Protecting Groups of Amino Sugars and Their Use in Glycoside Synthesis. 2-Nitrobenzyloxycarbonylamino and 6-Nitroveratryloxycarbonylamino Derivatives," J. Org. Chem. 39:192-196.
Arratia, R., et al., (1989) "Poisson Process Approximation for Repeats in One Sequence and Its Application to Sequencing by Hybridization," Dept. of Mathematics, University of Southern California.
Austin, M., et al., (2004) "Fabrication of 5 nm Linewidth and 14 nm Pitch Features by Nanoimprint Lithography," App. Phys. Lett. 84:5299-5301.
Bains, W., et al., (1988) "A Novel Method for Nucleic Acid Sequence Determination," J. Theor. Biol. 135:303-307.
Baliga, R., et al., (2001) "Kinetic Consequences of Covalent Linkage of DNA Binding Polyamides," Biochemistry 40:3-8.
Bennett et al. Pharmacogenomics (2005) 6:373-382.
Bianco, P., et al., "Interaction of the RecA Protein of *Escherichia coli* with Single-Stranded Oligodeoxyribonucleotides," Nucleic Acids Research vol. 24. No. 24 (1996) 4933-4939.
Buchmueller, K.L., et al., (2005) "Extending the Language of DNA Molecular Recognition by Polyamides: Unexpected Influence of Imidazole and Pyrrole Arrangement on Binding Affinity and Specificity," J. Am. Chem. Soc. 127:742-750.

(56) References Cited

OTHER PUBLICATIONS

Buchmueller, K.L., et. al., (2006) "Physical and Structural Basis for the Strong Interactions of the -ImPy- Central Pairing Motif in the Polyamide f-ImPyIm," Biochemistry 45:13551-13565.

Cao, H., et al., (2002) "Fabrication of 10 nm Enclosed Nanofluidic Channels," Applied Physics Letters 81(1): 174-176.

Cao, H., et al., (2002) "Gradient Nanostructures for Interfacing Microfluidics and Nanofluidics," Applied Physics Letters 81:3058-3060.

Chen, C., et al., (1994) "Analogous Organic Synthesis of Small-Compound Libraries: Validation of Combinatorial Chemistry in Small-Molecule Synthesis," J. Am. Chem. Soc. 116:2661-2662.

Chen, P., et al., (2004) "Probing Single DNA Molecule Transport Using Fabricated Nanopores," Nano Letters 4:2293-2298.

Chetverin, A., et al., (1994) "Oligonucleotide Arrays: New Concepts and Possibilities," Bio/Technology 12:1093-1099.

Cox, M. (2007) "Motoring Along with the Bacterial RecA Protein," Nature Reviews—Molecular Cell Biology 9:127-138.

Dervan, P.B. (2001) "Molecular Recognition of DNA by Small Molecules," Bioorg. Med. Chem. 9:2215-2235.

Dervan, P.B., et al., (2003) "Recognition of the DNA minor groove by pyrrole-imidazole polyamides," Curr. Op. Struc. Biol. 13:284-299.

Doss, R.M., et al., (2006) "Programmable Oligomers for Minor Groove DNA Recognition," J. Am. Chem. Soc. 128:9074-9079.

Drmanac, R., et al. (1989) "Sequencing of Megabase Plus DNA by Hybridization: Theory of the Method," Genomics 4:114-128.

Ellervik, U., et al., (2000) "Hybroxybenzamide/Pyrrole Pair Distinguishes T-A from A-T Base Pairs in the Minor Groove of DNA," J. Am. Chem. Soc. 122:9354-9360.

Farkas, Z., et al., (2003) "DNA Uptake Into Nuclei: Numerical and Analytical Results," J. Phys.: Condens. Matter 15:S1767-S1777.

Fechter, E.J., et al., (2005) "Sequence-specific Fluorescence Detection of DNA by Polyamide-Thiazole Orange Conjugates," J. Am. Chem. Soc. 127:16685-16691.

Floreancig, P.E., et al., (2000) "Recognition of the Minor Groove of DNA by Hairpin Polyamides Containing α-Substituted-,β-Amino Acids," J. Am. Chem. Soc. 122:6342-6350.

Fodor, S., et al., (2005) "Light-Directed, Spatially Addressable Parall Chemical Synthesis" Research Article 6 pgs.

Fologea, D., et al., (2005) "Slowing DNA Translocation in a Solid-State Nanopore," Nano Lett. 5(9):1734-7.

Frieze, A., et al., (1999) "Optimal Reconstruction of a Sequence From its Probes," 12 pgs.

Gerland, U., et al., (2004) "Translocation of Structured Polynucleotides Through Nanopores," Phys. Biol. 1:19-26.

Gershow, M., et al., (2007) "Recapturing and Trapping Single Molecules with a Solid-State Nanopore," Nature Nanotech. 2:775-779.

Gracheva, M., et al., (2002) "Simulation of the Electric Response of DNA Translocation through a Semiconductor Nanopore-Capacitor," Nanotechnology 17:622-633.

Guo, L. (2004) "Recent Progress in Nanoimprint Technology and its Application," J. Phys. D: Appl. Phys 37:R123-R141 (Appendices B-D).

Gygi, M.P., et al., (2002) "Use of fluorescent sequence-specific polyamides to discriminate human chromosomes by microscopy and flow cytometry," Nucleic Acids Research 30:2790-2799.

Halby, L., et al., (2005) "Functionalized head-to-head hairpin polyamides: Synthesis, double-stranded DNA-binding activity and affinity," Bioorg. Med. Chem. Lett. 15:3720-3724.

Heller, C., (2001) "Principles of DNA Separation with Capillary Electrophoresis," Electrophoresis 22:629-643.

Heng, J., et al., (2004) "Sizing DNA Using a Nanometer-Diameter Pore," Biophysical Journal 87:2905-2911.

Hudson, B., (1999) "An Experimental Study of SBH with Gapped Probes," 50 pgs.

International Search Report and Written Opinion dated May 2, 2009, PCTUS2008/078432.

Jonsson, U., et al., (1991) "Real-Time Biospecific Interaction Analysis Using Surface Plasmon Resonance and a Sensor Chip Technology," BioTechniques, 11:620-627.

Ju et al., Proc. Nat. Acad. Sci. USA (2006) 103:19635-19640.

Kalaugher, L., (2002) "Diffraction Gradient Lithography Aids Nanofluidics," Nanotechweb.org.

Kanehisa, L. (1984) "Use of Statistical Criteria for Screening Potential Homologies in Nucleic Acid Sequences," Nucleic Acids Research 12:203-213.

Kasianowicz et al., "Characterization of Individual Polynucleotide Molecules Using a Membrane Channel," Proc. Nat. Acad. Sci. USA 93:13770-13773 (1996).

Khrapko, K.R. et al., (1989) "An Oligonucleotide Hybridizatioin Approach to DNA Sequencing," FEBS Lett. 256:118-22.

Kim, C., et al., (1992) "Binding Properties of Replication Protein a from Human and Yeast Cells," Mol. and Cell. Bio. 12(7):3050-3059.

Liang, X., et al., (2007) "Single Sub-20 nm wide Centimeter-Long NanoFluidic Channel Fabricated by Novel Nanoimprint Mold Fabrication and Divest Imprinting," Nano Letters 7:3774-3780.

Liang, X., et al., (2008) "Nanogap Detector Inside Nanofluidic Channel for Fast Real Time Label-Free DNA Analysis," Nano Letters 8:1472-76.

Ling, X., et al., "Hybridization Assisted Nanopore Sequencing," Patent Specification, 32 pgs.

Loakes, D., et al., (1994) "5-Nitroindole as an Universal Base Analogue," Nucleic Acids Research 22:4039-4043.

Loakes, D., et al., (1995) "3-Nitropyrrole and 5-Nitroindole as Universal Bases in Primers for DNA Sequencing and PCR," 23:2361-2366.

Lohman, T., et al., (1994) "*Escherichia Coli* Single-Stranded DNA-Binding Protein: Multiple DNA-Binding Modes and Cooperatives," Annu. Rev. Biochem. 63:527-70.

Lysov, Y.P., et al., (1988) "Determination of the Nucleotide Sequence of DNA Using Hybridization with Oligonucleotides. A New Method," Dokl. Acad. Nauk SSSR 303:1508-1511 [Article in Russian].

Margulies et al., (2005) Nature 437:376-380.

Marques, M.A., et al., (2004) "Expanding the Repertoire of Heterocycle Ring Pairs for Programmable Minor Groove DNA Recognition," J. Am. Chem. Soc. 126:10339-10349.

McEntee, K., et al. "Binding of the RecA Protein of *Escherichia coli* to Single- and Double-Stranded DNA." J. Biol. Chem. (1981) 256:8835.

Meller, A., et al., (2000) "Rapid Nanopore Discrimination Between Single Polynucleotide Molecules," PNAS 97:1079-1084.

Nice, E., et al., (1993) "Mapping of the Antibody- and Receptor-Binding Domains of Granulocyte Colony-Stimulating Factor Using an Optical Biosensor," Journal of Chromatography 646:159-168.

Nichols, R., et al., (1994) "A Universal Nucleoside for Use at Ambiguous Sites in DNA Primers," Letters to Nature 369:492-493.

Novopashina, D.S., et al., (2005) "Sequence-Specific Conjugates of Oligo(2'-O-methylribonucleotides) and Hairpin Oligocarboxamide Minor-Groove Binders: Design, Synthesis, and Binding Studies with Double-Stranded DNA," Chemistry & Biodiversity 2:936-952.

Pablo, P.J., et al., (2000) "Absence of dc-Conductivity." Phys. Rev. Lett. 85:4992-4995.

Perry, J., et al., (2005) "Review of Fabrication of Nanochannels for Single Phase Liquid Flow," 3rd Intl. Conference on Microchannels and Minichannels, Paper No. ICMM2005-75104.

Pevzner, P. et al., (1991) "Improved Chips for Sequencing by Hybridization," Journal of Biomolecular Structure & Dynamics 9:399-410.

Pevzner, P., (1989) "1-Tuple DNA Sequencing: Computer Analysis," Journal of Biomolecular Structure & Dynamics 7:63-73.

Powell, M., et al., (1993) "Characetrization of the Pf3 Single-Strand DNA Binding Protein by Circular Dichroism Spectroscopy," Biochemistry 32:12538-12547.

Preparata, F., et al. (1999) "On the Power of Universal Bases in Sequencing by Hybridization," 7 pgs.

Preparata, F.P., et. al., (2000) "Sequencing-by-Hybridization at the Information-Theory Bound: An Optimal Algorithm," J. Comp. Biol. 7: 621-630.

Quake et al. Proc. Nat. Acad. Sci. USA (2003) 100:3960-3964.

Riehn, R. et al., (2005) Proc. Nat. Acad. Sci., 102:1012.

Robertson, J., et al., (2007) "Single-Molecule Mass Spectrometry in Solution Using a Solitary Nanopore," PNAS 104:8207-8211.

(56) References Cited

OTHER PUBLICATIONS

Rucker, V.C., et al., (2003) "Sequence Specific Fluorescence Detection of Double Strand DNA," J. Am. Chem. Soc. 125:1195-1202.
Sanger, F. et al., (1977) "DNA Sequencing with Chain-Terminating Inhibitors," Proc. Natl. Acad. Sci. USA 12:5463-5467.
Shinohara. Y., et al., (1995) "Use of a Biosensor Based on Surface Plasmon Resonance and Biotinyl Glycans for Analysis of Sugar Binding Specificities of Lectins," J. Biochem, 117:1076-1082.
Singer, E. (2008) "The $100 Genome," Technology Review 4 pgs.
Smeets, R., et al., (2008) "Translocation of RecA-Coated Double-Stranded DNA through Solid-State Nanopores," Nano Letters pp. A-G.
Southern, E.M. (1996) "DNA Chips: Analysing Sequence by Hybridization to Oligonucleotide on a Large Scale," Trends in Genetics 12(3):110-115.
Storm, A., et al., (2005) "Fast DNA Translocation through a Solid-State Nanopore," Nano Letters 5(7):1193-1197.
Strezoska, Z., et al., (1991) "DNA Sequencing by Hybridization: 100 Bases Read by a Non-Gel-Based Method," Proc. Natl. Acad. Sci. USA 88:10089-10093.
Tegenfeldt, J., et al., (2004) "The Dynamics of Genomic-Length DNA Molecules in 100 nm Channels," Proc. Nat. Acad. Sci. USA 101:10979-10983.
Terwilliger, T., et al., (1996) "Gene V Protein Dimerization and Cooperativity of Binding to Poly (dA)," Biochemistry 35:16652-16664.
Tucker, P., et al., (1994) "Crystal Structure of the Adenovirus DNA Binding Protein a Hook-On Model for Cooperative DNA Binding," The EMBO Journal 13(13):2994-3002.
Urbach, A.R., (2001) "Toward rules for 1:1 polyamide:DNA recognition," PNAS 98:4343-4348.
Warren, C.L., et al., (2006) "Defining the Sequence-Recognition Profile of DNA-Binding Molecules," PNAS 103:867-872.
Warren, S., (1996) "The Expanding World of Trinucleotide Repeats," Science 271:1374-1375.
Web article (2003) "DNA Combed Into Nanochannels," http://www.nature.com.
Written Opinion dated Jul. 1, 2008, PCT/US06/38748.
Zhang, W., et al., (2006) "Discrimination of Hairpin Polyamides with an α-Substituted-γ-aminobutyric Acid as a 5'-TG-3' Reader in DNA Minor Groove," J. Am. Chem. Soc. 128:8766-8776.
Zwolak, M., et al., (2008) "Physical Approaches to DNA Sequencing and Detection." Rev. Mod. Phy. 80:141-165 (J).
Giehart B., et al., (2008) "Nanopore with transverse nanoelectrodes for electrical characterization and sequencing of DNA" Sensors and Actuators B., Elsevier Sequoia S.A, ScienceDirect,132:2.
International Search Report and Written Opinion for PCT/US09/558876 dated Jun. 29, 2010 (13 pages).
Invitation to Pay Additional Fees and, Where Applicable, Protest Fee & Partial International Search dated Aug. 19, 2010, PCT/US2010/028848, 7 pages.
Ghosh, et al, Direct detection of double-stranded DNA: molecular methods and applications for DNA diagnostics, Molecular BioSystems, 2006, 551-560, 10 pages.
International Preliminary Report on Patentability dated Sep. 30, 2011, PCT/US2009/055876, 7 pages.
International Search Report and Written Opinion dated Sep. 30, 2010, PCT/US2010/028848, 14 pgs.
International Search Report and Written Opinion dated Mar. 24, 2010 for PCT/US09/055878, 13 pages.
Optical Tweezers: Introduction to Optical Tweezers, Retrieved Apr. 21, 2010 from http://www.nbl.dk/~tweezer/introduction.htm, pp. 1.5.
Tersoff, "Less is more," Nature 412, 135-136, Jul. 2001.
Bloom et al., Applications of Numbered Undirected Graphs, Proceedings of the IEEE, vol. 65, No. 4, Apr. 1977, pp. 562-570.
International Preliminary Report on Patentability, Application No. PCT/US2009/055876, issuance date Mar. 8, 2011, 6 pages.
International Preliminary Report on Patentability, Application No. PCT/US2008/078432, issuance date Apr. 7, 2010, 6 pages.
International Preliminary Report on Patentability, Application No. PCT/US2010/028848, issuance date Sep. 27, 2011, 8 pages.
International Preliminary Report on Patentability, Application No. PCT/US2009/055878, issuance date Nov. 29, 2011, 9 pages.
International Preliminary Report on Patentability, Application No. PCT/US2011/053274, issuance date May 28, 2013, 14 pages.
International Preliminary Report on Patentability, Application No. PCT/US2011/059933, issuance date May 21, 2013, 8 pages.
International Search Report and Written Opinion, PCT/US2011/053274, dated May 2, 2013.
Drmanac, R., et al. (2002) "Sequencing by Hybridization (SBH): Advantages, Achievements, and Opportunities," Advances in Biochemical Engineering/Biotechnology, vol. 77: 75-101.
International Search Report and Written Opinion dated Feb. 5, 2009, PCT/US08/078432.
Invitation to Pay Additional Fees and, Where Applicable, Protest Fee & Partial International Search dated Jul. 10, 2012, PCT/US2012/024708, 10 pages.
Ben-Dor et al, "On the Complexity of Positional Sequencing by Hybridization", Journal of Computational Biology, vol. 8, No. 4, 2001, pp. 361-371.
Branton, Daniel et al, "The potential and challenges of anopore sequencing," Nature Biotechnology, vol. 26, No. 10, Oct. 2008, pp. 1146-1153.
International Search Report and Written Opinion, PCT/US2011/059933, dated Apr. 2, 2012, 13 Pages.
Anderson, P. et al., "Nkx3.1 and Myc crossregulate shared target genes in mouse and human prostate tumorigenesis," J. Clinical Investigation, May 2012, pp. 1907-1919, vol. 122, http://www.jci.org.
Arrowsmith, C. et al., "Epigenetic protein families: a new frontier for drug discovery," Nature Reviews: Drug Discovery, May 2012, pp. 384-400, vol. 11, Macmillan Publishers Limited.
Austin, Robert, "The art of sucking spaghetti", Nature Publishing Group, Nature Materials, vol. 2, pp. 567-568, Sep. 2003.
Bourdoncle, A., et al., "Quaruplex-Based Molecular Beacons as Tunable DNA Probes", J. Am. Chem. Soc., vol. 128, No. 34, pp. 11094-11105, 2006.
Examination Report mailed Feb. 7, 2013 in European Application No. 10 717 908.7-1240 (4 pages).
Examination Report mailed Mar. 4, 2013 in European Application No. 08 835 216.6-1404 (6 pages).
Greer, E. et al., "Histone methylation: a dynamic mark in health, disease and inheritance," Nature Review: Genetics, May 2012, pp. 343-357, vol. 13, Macmillan Publishers Limited.
Hannenhalli S. et al. Comput Appl Biosci (1996) 12 (1): 19-24.
Heyn, H. et al., "DNA methylation profiling in the clinic: applications and challenges," Nature Review: Genetics, Oct. 2012, pp. 679-692, vol. 13, Macmillan Publishers Limited.
International Preliminary Report on Patentability in PCT/US2012/024708 mailed Aug. 22, 2013.
International Search Report and Written Opinion dated Oct. 25, 2012, PCT/US12/024708.
International Search Report and Written Opinion for PCT/US09/558876 dated Jun. 29, 2010, 10 pages.
Invitation to Pay Additional Fees and, Where Applicable, Protest Fee & Partial International Search dated Feb. 15, 2013, PCT/US2011/053274, 9 pages.
Koike, Shinji et al., "Investigation into the Degrading Mechanism of Positive Electrodes after Calendar Life Test Using Transmission Electron Microscopy", 214th ECS Meeting, Abstract #569, The Electrochemical Society, Osaka, Japan, 1 page.
Langer-Safer, P. et al., "Immunological method for mapping genes on *Drosophila* polytene chromosomes," Proc. Natl. Acad. Sci. USA, Jul. 1982, pp. 4381-4385, vol. 79.
Lennon, Erwan et al., "Evaporative Pumping of Liquid in Nanochannel for Electrical Measurement of a Single Biomolecule in Nanofluidic Format", Proceedings of the 7th IEEE Internation Conference on Nantechnology, Hong Kong, Aug. 2-5, 2007.
Notice of Reasons for Rejection mailed Jun. 17, 2013 in Japanese Patent Application No. 2011-525300.
Notification of the First Office Action mailed Sep. 28, 2012 in Chinese Patent Application No. 200980140663.0.

(56) References Cited

OTHER PUBLICATIONS

Notification of the Second Office Action mailed Apr. 2, 2013 in Chinese Patent Application No. 200980140663.0.
Park, P., "ChIP-seq: advantages and challenges of a maturing technology," Nature Reviews: Genetics, Oct. 2009, pp. 669-680, vol. 10, Macmillan Publishers Limited.
Pastor, W. et al., "Genome-wide mapping of 5-hydroxymethylcytosine in embryonic stem cells," Nature, May 19, 2011, pp. 394-397, vol. 473, Macmillan Publishers Limited.
Rapley, Ralph, "Enhancing PCR Amplification and Sequencing Using DNA-Binding Proteins", Molecular Biotechnology, vol. 2, pp. 295-298, 1994.
Rehrauer, William M. et al., "Alteration of the Nucleoisude Triphosphate (NTP) Catalytic Domain within *Escherichia coli* recA Protein Attenuates NTP Hydrolysis but Not Joint Molecule Formation", pp. 1292-1297, The Journal of Biological Chemistry, The American Society for Biochemistry and Molecule Biology, Inc., vol. 268, No. 2, Jan. 15, 1993.
Riccelli, P. V. et al., "Hybridization of single-stranded DNA targets to immobilized complementary DNA probes: comparison of hairpin versus linear capture probes", Oxford University Press, Nucleic Acids Research, vol. 29, No. 4, pp. 996-1004, 2001.
Ross-Innes, C. et al., "Differential oestrogen receptor binding is associated with clinical outcome in breast cancer," Nature, Jan. 2012, pp. 389-394, vol. 481, Macmillan Publishers Limited.
Salpea, P. et al., "Postnatal development- and age-related changes in DNA-methylation patterns in the human genome," Nucleic Acids Research, 2012, pp. 6477-6494, vol. 40, No. 14, Oxford University Press.
Shoaib, M. et al., "Pub-NChIP-"In vivo biotinylation" approach to study chromatin in proximity to a protein of interest," Genome Research, 2013, pp. 331-340, vol. 23, Cold Spring Harbor Laboratory Press, www.genome.org.
van Steensel, B. et al., "Identification of in vivo DNA targets of chromatin proteins using tethered Dam methyltransfarase," Nature Biotechnology, Apr. 2000, pp. 424-428, vol. 18.
Waugh, David S., "Make the most of affinity tags", pp. 316-320, Trends in Biotechnology, Science Direct, vol. 23, No. 6, Jun. 2005.
Broude et al. (1994) Enhanced DNA sequencing by hybridization, Proc. Natl. Acad. Sci. USA, 91, 3072-3076.
Invitation to Pay Additional Fees And, Where Applicable, Protest Fee & Partial International Search dated Mar. 3, 2014, PCT/US2012/061651, 5 pages.
Olasagasti, F.; Lieberman, K. R.; Benner, S.; Cheri, G. M.; Dahl, J. M.; Deamer, D. W.; Akeson, M. *Nat. Nanotechnol.* 2010, 5, 798-806.
Rapley, Ralph, "Direct Sequencing of PCR Products with DNA-Binding Proteins", Methods in Molecular Biology, vol. 65, Humana Press Inc., Totowa, NJ, pp. 101-104.
Shim et al., "Detection and Quantification of Methylation in DNA using Solid-State Nanopores", Scientific Reports, www.nature.com, Mar. 11, 2013, pp. 1-8.
Venkatesan et al., "Stacked Graphene-Al2O3 Nanopore Sensors for Sensitive Detection of DNA and DNA-Protein Complexes", www.acsnano.org, vol. 6, No. 1, 2012, pp. 441-450.
Stephen et al., "DNA manipulation sorting, and mapping in nanofluidic systems," Chemical Society Reviews, vol. 39, No. 3, Jan. 1, 2010, p. 1133.
Wu et al., "On-column conductivity detection in capillary-chip electrophoresis", 2007, 28, 4612-4619.
International Search Report and Written Opinion dated Jun. 26, 2014, PCT/US14/011829, 14 pages.
Notice of Final Rejection mailed Jul. 2, 2014 in Japanese Patent Application No. 2011-525300.

\* cited by examiner

SEQUENCE LISTING

```
<160> NUMBER OF SEQ ID NOS: 2

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cttctagatt ctag                                                    14

<210> SEQ ID NO 2
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cuucuagauu cuag                                                    14
```

USE OF LONGITUDINALLY DISPLACED NANOSCALE ELECTRODES FOR VOLTAGE SENSING OF BIOMOLECULES AND OTHER ANALYTES IN FLUIDIC CHANNELS

RELATED APPLICATION

This application claims the benefit of priority under 35 U.S.C. §119(e) to U.S. Provisional Ser. No. 61/093,885, filed Sep. 3, 2008; the entirety of which is incorporated herein by reference.

SEQUENCE LISTING

The instant application contains a Sequence Listing which has been submitted via EFS-Web and is hereby incorporated by reference in its entirety. Said ASCII copy, created on Oct. 1, 2009, is named NAB001.txt, and is 974 bytes in size.

FIELD OF INVENTION

The present invention relates generally to biopolymer sequencing. More particularly, in certain embodiments, the invention relates to determining the length of biopolymers and the distances of probes bound to the biopolymer.

BACKGROUND

The technique known as Coulter counting was first proposed by Wallace H. Coulter in the late 1940s as a technique for the high speed counting of red blood cells. Also referred to as resistive pulse sensing, Coulter counting may be used to measure physical parameters of analytes in electrolyte solution including size (volume), charge, electrophoretic mobility and concentration. In this technique, two reservoirs of solution are separated by a fluidic constriction of known dimensions. The application of a constant DC voltage between the two reservoirs results in a baseline ionic current that is measured. The magnitude of the baseline current is related to the conductivity of the electrolyte, the applied potential, the length of the channel, and the cross-sectional area of the channel. If an analyte is introduced into a reservoir, it may pass through the fluidic channel and reduce the observed current due to a difference in conductivity between the electrolyte solution and analyte. The magnitude of the reduction in current depends on the volume of electrolyte displaced by the analyte while it is in the fluidic channel.

A benefit of the resistive pulse sensing technique is that it may be scaled down to enable the detection of nanoscale analytes through the use of nanoscale fluidic constrictions. This capability led to the development of solid-state nanopores for detecting nanoscale molecules such as DNA.

In the case of DNA translocation through a nanopore, the physical translocation is driven by the electrophoretic force generated by the applied DC voltage. This driving force and the detected signal are, therefore, typically inseparably coupled. The decoupling of these two effects may be desirable because the optimal potential for physical translocation is different from that of optimal measurement.

Transverse electrodes have been proposed to provide a transverse electric field and electric current to sense biomolecules confined in a nanofluidic channel. See Liang and Chou 2008 Liang, X; Chou, S. Y., *Nanogap Detector Inside Nanofluidic Channel for Fast Real-Time Label-Free DNA Analysis*. Nano Lett. 2008, 8, 1472-1476, which is incorporated herein by reference in its entirety. The analytes are moved through the channel with an electrophoretic force generated by current-carrying electrodes at the ends of the nanochannel, therefore decoupling the measurement from the translocation speed.

SUMMARY

Embodiments of the present invention provide devices and methods that use electrodes to sense voltage changes, rather than to generate transverse electric currents, thereby reducing degradation of the electrodes. In particular, a device described herein utilizes longitudinally displaced electrodes for electronic sensing of biomolecules and other nanoscale analytes in fluidic channels. Embodiments enable characterization of nanoscale analytes, including, e.g., analysis of DNA strands having probes attached thereto.

More particularly, embodiments of the present invention may utilize sensing electrodes for electronic sensing of analytes, e.g., DNA, in fluidic channels. The sensing electrodes in the fluidic channel may be used to determine the length of the analyte or they may be used to determine the distance between probes hybridized to a target strand of DNA. The device design is similar to nanochannel devices used for optical detection. Two micro-scale liquid reservoirs may be fabricated at a distance of 100 to 200 µm. One or more fluidic channels may connect the two reservoirs. A cap may be fabricated by drilling holes that will allow fluid introduction to each reservoir and to provide access for macroscopic electrodes. In use, a voltmeter may be used to monitor the potential difference between two sensing electrodes.

The DNA to be analyzed may be introduced to one of the microfluidic reservoirs. Macroscopic electrodes may be connected to a power supply and used to apply a potential between the two reservoirs. DNA fragments may be electrophoretically driven from the microscopic reservoir into the nanochannels. As each DNA fragment moves down the fluidic channel, it may enter and exit the pair of sensing electrodes disposed in the fluidic channel.

In the absence of DNA, the fluidic channel contains only the ionic solution and typically have a baseline potential difference measured between the two sensing electrodes. As DNA enters the fluidic channel, the potential measured between the two sensing electrodes may change because the DNA has a conductivity different from that of the ionic solution. When DNA enters the fluidic channel, the conductivity of the channel between the two sensing electrodes will typically be reduced as DNA is less conductive than the buffer solution (See de Pablo, P. J.; Moreno-Herrero, F; Colchero, J.; Gomez-Herrero, J.; Herrero, P.; Baro, A. M.; Ordejon, P.; Soler, J. M.; Artacho, E. Absence of dc-Conductivity in *Phys. Rev. Lett.* 2000, 85, 4992-4995, which is incorporated by reference in its entirety). When a portion of the DNA that has a probe hybridized to the DNA enters the fluidic channel the potential may change further. The measured signal may be analyzed to determine the length of the DNA and/or distances between probes.

In an aspect, an embodiment of the invention includes a device for voltage sensing of analytes. The device may include a fluidic channel defined in a substrate, and a pair of sensing electrodes disposed in the fluidic channel for sensing voltage therein. The pair of sensing electrodes may include a first and a second sensing electrode disposed at two discrete locations along a length of the fluidic channel. A pair of electromotive electrodes may be disposed at a first end and a second end of the fluidic channel for applying a potential along the fluidic channel. The fluidic channel may include or consist essentially of a nanochannel or a microchannel.

One or more of the following features may be included. The substrate may include or consist essentially of silicon, silicon dioxide, fused silica, and/or gallium arsenide. Each of the sensing and electromotive pairs of electrodes may include or consist essentially of platinum, gold, chrome, titanium, silver chloride, silver, and graphene.

The first sensing electrode may be disposed on a first side of the fluidic channel and the second sensing electrode may be disposed on an opposing side of the fluidic channel. Each of the first and second sensing electrodes may be disposed on a first side of the fluidic channel, or each of the first and second sensing electrodes may transverse the fluidic channel. The first sensing electrode may transverse the fluidic channel and the second sensing electrode may be disposed on a side of the fluidic channel.

The pair of electromotive electrodes may include macroscopic electrodes for generating a constant, changing, or oscillating electrophoretic force in the fluidic channel for translocation of an analyte disposed therein.

A measurement tool, such as a voltmeter, may be provided for measuring a voltage sensed by the pair of sensing electrodes. The device may include a plurality of fluidic channels. A voltage amplifier may be disposed on the substrate.

The fluidic channel may have a width selected from a range of 1 nm to 5 µm, a depth selected from a range of 1 nm to 5 µm, and/or a length selected from a range of 1 µm to 10 cm.

The description of elements of the embodiments of other aspects of the invention may be applied to this aspect of the invention as well.

In another aspect, the invention features a method for detecting an analyte, the method including disposing the analyte in a fluidic channel. A potential is applied along the fluidic channel and the analyte is translocated from a first end of the fluidic channel to a second end of the fluidic channel. A voltage signal is measured between a pair of sensing electrodes disposed in the fluidic channel as the analyte moves past the pair of sensing electrodes, with the pair of sensing electrodes including a first and a second electrode disposed at two discrete locations along a length of the fluidic channel. The fluidic channel may include or consist essentially of a nanochannel or a microchannel.

The potential applied along the fluidic channel may include generating an electrophoretic force therein. Translocating the analyte may include using a pressure differential and/or a chemical gradient.

One or more of the following features may be included. The analyte may include a biopolymer, such as a deoxyribonucleic acid, a ribonucleic acid, and/or a polypeptide. The biopolymer may include or consist essentially of a single-stranded molecule. The analyte may include or consist essentially of a biopolymer having at least one probe attached thereto.

The voltage signal may change when the biopolymer moves through a volume between the sensing electrodes and further change when the portion of the biopolymer containing the probe moves through the volume between the sensing electrodes. A time between voltage signal changes may be recorded. A duration of a change in the voltage signal may indicate a presence of a probe, and the voltage signal may be used to determine a distance between two probes on the biopolymer.

A duration of a change in the voltage signal may be used to determine a length of the analyte. Multiple pairs of sensing electrodes may be used to measure a single analyte molecule as it passes through the fluidic channel.

The description of elements of the embodiments of other aspects of the invention may be applied to this aspect of the invention as well.

In yet another aspect, a method for determining a sequence of a biopolymer may include preparing an analyte including the biopolymer. The analyte may be disposed in a fluidic channel. A potential may be applied along the fluidic channel and the analyte is translocated from a first end of the fluidic channel to a second end of the fluidic channel. A voltage signal may be measured between a pair of sensing electrodes disposed in the fluidic channel as the analyte moves past the pair of sensing electrodes, the voltage signal corresponding to locations along the biopolymer, the pair of sensing electrodes including a first and a second electrode disposed at two discrete locations along a length of the fluidic channel. The fluidic channel may include or consist essentially of a nanochannel or a microchannel.

The potential applied along the fluidic channel may include generating an electrophoretic force therein. The analyte may be translocated by using a pressure differential and/or a chemical gradient.

One or more of the following features may be included. Preparing the analyte may include hybridizing the biopolymer with a probe. A change in the voltage signal may correspond to a location along the hybridized biopolymer containing the probe. The voltage signal may be processed using a computer algorithm to reconstruct the sequence of the biopolymer. The biopolymer may include or consist essentially of a double-stranded biopolymer target molecule. Preparing the analyte may include contacting the target molecule with a first probe having a first probe specificity for recognition sites of the target molecule to form a first plurality of local ternary complexes, the first probe having a first predicted recognition site sequence. The voltage signal may be used to determine positional information of the first plurality of local ternary complexes. The positional information may include a parameter to a spatial distance between two local ternary complexes.

Preparing the analyte may further include contacting the target molecule with a second probe having a second probe specificity for recognition sites of the target molecule to form a second plurality of local ternary complexes, the second probe having a second predicted recognition site sequence.

The voltage signal may be used to determine positional information of the second plurality of local ternary complexes. Positional information of at least the first and second plurality of local ternary complexes may be aligned to determine a DNA sequence of the target.

The biopolymer may include or consist essentially of a double-stranded nucleic acid target molecule having a plurality of binding sites disposed along the sequence thereof. Preparing the analyte may include adding a plurality of probe molecules having a first sequence specificity to the double stranded nucleic acid target molecule.

The probe molecules having the first sequence specificity and the target molecule may be incubated so as to effectuate preferential binding of the first probe molecules to both a first binding site and a second binding site of the target molecule. The voltage signal may be used to measure a parameter related to a distance between the first binding site and the second binding site.

Preparing the analyte may include contacting the biopolymer with a first probe to create at least one probe-target complex at a recognition site of the biopolymer for which the first probe has a known specificity, while leaving uncomplexed, regions of the biopolymer for which the first probe is not specific. Preparing the analyte may include contacting the biopolymer with a second probe to create at least one probe-target complex at a recognition site of the biopolymer for which the second probe has a known specificity, while leaving uncomplexed, regions of the target for which the second probe is not specific.

The voltage signal may be used to detect and record complexed and uncomplexed regions of the biopolymer to create a first probe map of the first probe and a second probe map of the second probe, the first probe map and the second probe map incorporating information on the relative position of the hybridization of the probes. A candidate sequence may be determined by aligning at least two probe sequences using positional information or a combination of overlapping sequences of the probe molecules and positional information. The first and second probe maps may incorporate information on an error of the positional information for each probe. A candidate sequence may be determined by ordering at least two probe sequences using positional information and parameters relating to the error in positional information or a combination of overlapping sequences of the probe molecules and positional information and error in positional information.

The description of elements of the embodiments of other aspects of the invention may be applied to this aspect of the invention as well.

DETAILED DESCRIPTION

Fabrication of Fluidic Channel and Sensing Electrodes

Figure 1:
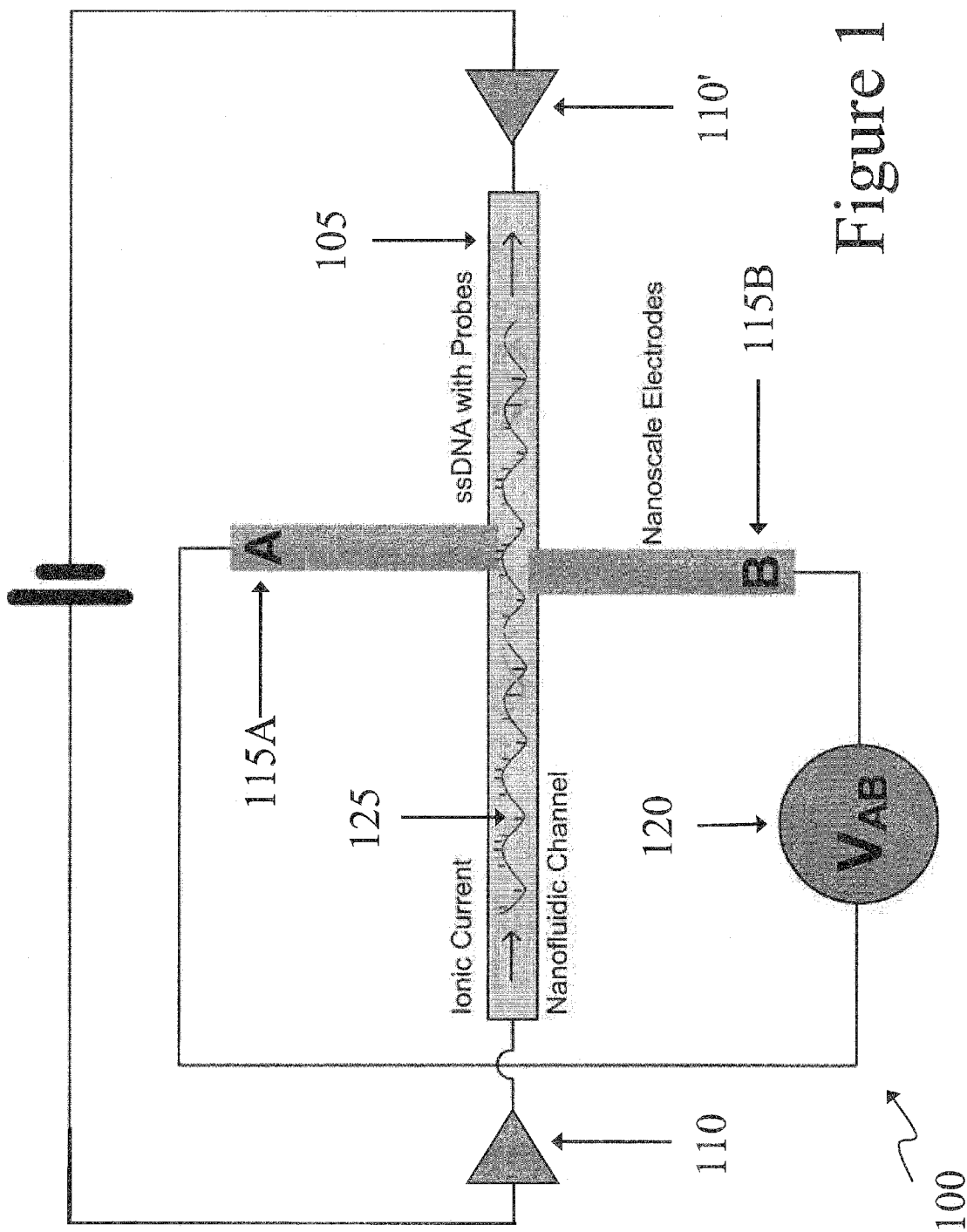
FIG. 1 is a schematic diagram illustrating a longitudinally displaced transverse electrode device configuration in accordance with an embodiment of the invention.

Embodiments of the invention include devices and methods for performing sequence analysis by hybridization ("SBH"). Referring to FIG. 1, in an embodiment a device 100 includes a fluidic channel 105, e.g., a micro- or nanochannel. A pair of electromotive electrodes 110, 110' are disposed at a first and a second end of the fluidic channel 105 for applying a potential along the fluidic channel. A pair of sensing electrodes 115A, 115B are disposed at two discrete locations along a length of the fluidic channel. The sensing electrodes may be in electrical communication with a measurement tool 120 that measures a voltage sensed by the sensing electrodes. The fluidic channel 105 may be defined in a substrate comprising either silicon, silicon dioxide, fused silica, or gallium arsenide, and may contain an electrolytic solution. The electromotive electrode pair 110, 110' may include at least one anode 110' and cathode 110' in contact with the electrolytic solution to provide a constant or changing current to drive the analyte 125 through the fluidic channel 105. In an alternate embodiment, a pressure differential, such as a positive pressure, may be used to drive the analyte 125 through the fluidic channel 105. Pressure may be supplied with a fluid pump or with a pressurized gas line. Other methods of applying pressure may be envisioned by one of skill in the art. In some embodiments, a chemical potential gradient may be used to move molecules through the fluidic channel 105. The analyte may also be translocated by using a chemical potential gradient. Chemical potential gradients may be created with concentration gradients. For instance, a fluidic channel may have one end immersed in a fluid that has a higher salt concentration than the fluid at the other end of the channel. The differential in salt concentration at the ends of the fluidic channel causes an osmotic pressure that can drive analytes through the channel.

As the analyte 125, which may be any biopolymer including, but not limited to, polypeptides, DNA or RNA, passes through the fluidic channel 105, it will pass between the pair of sensing electrodes 115A, 115B (each individually referred to herein as "A" and "B"). The sensing electrodes 115A, 115B contacting the fluidic channel 105 may be used to measure the changes in conductance of the electrolytic volume between them. The changes in conductance between the sensing electrodes 115A, 115B may be measured using a measurement tool 120, e.g., a voltmeter.

Figure 2:
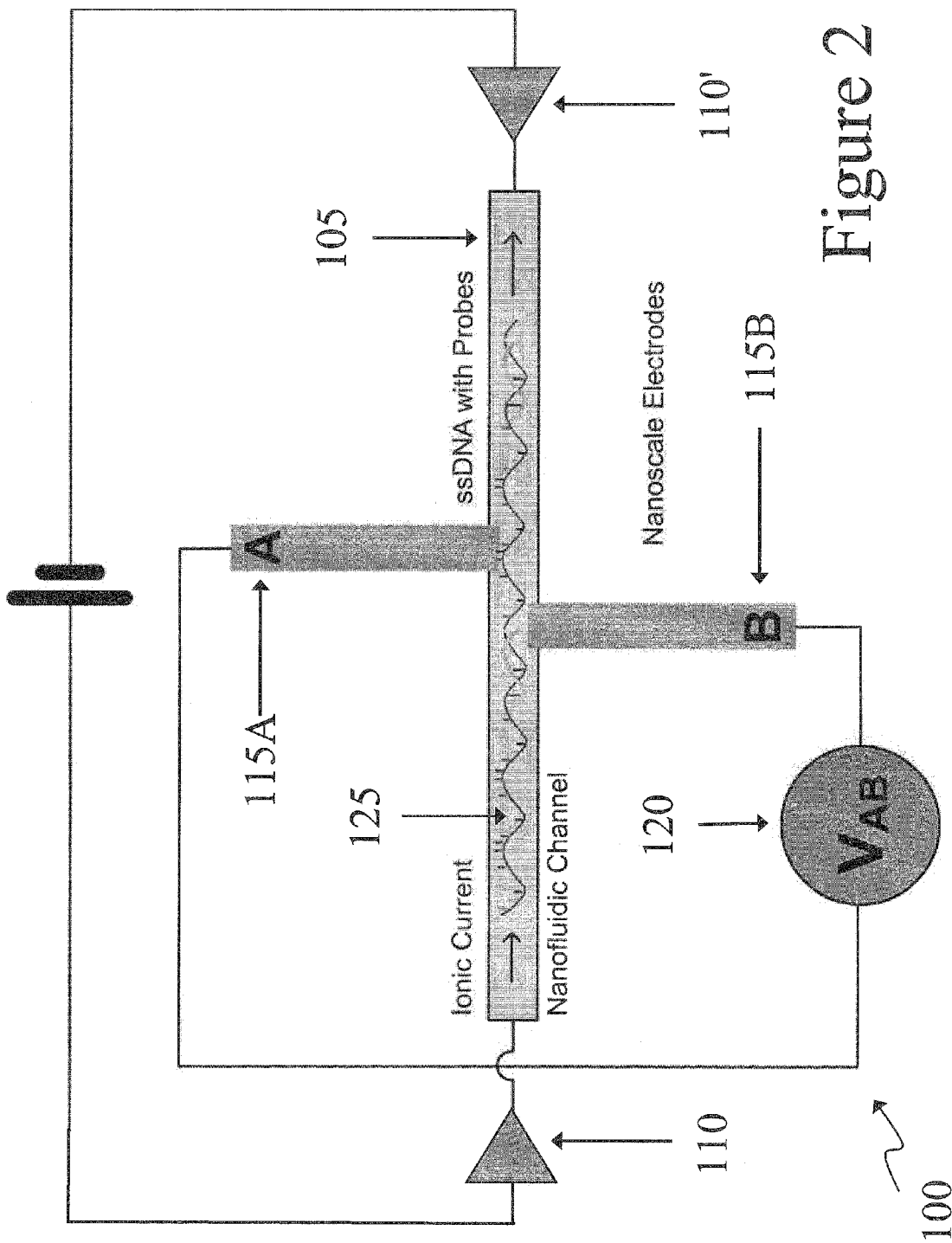
FIG. 2 is a schematic diagram illustrating a longitudinally displaced transverse electrode device configuration in accordance with another embodiment of the invention.
Figure 3:
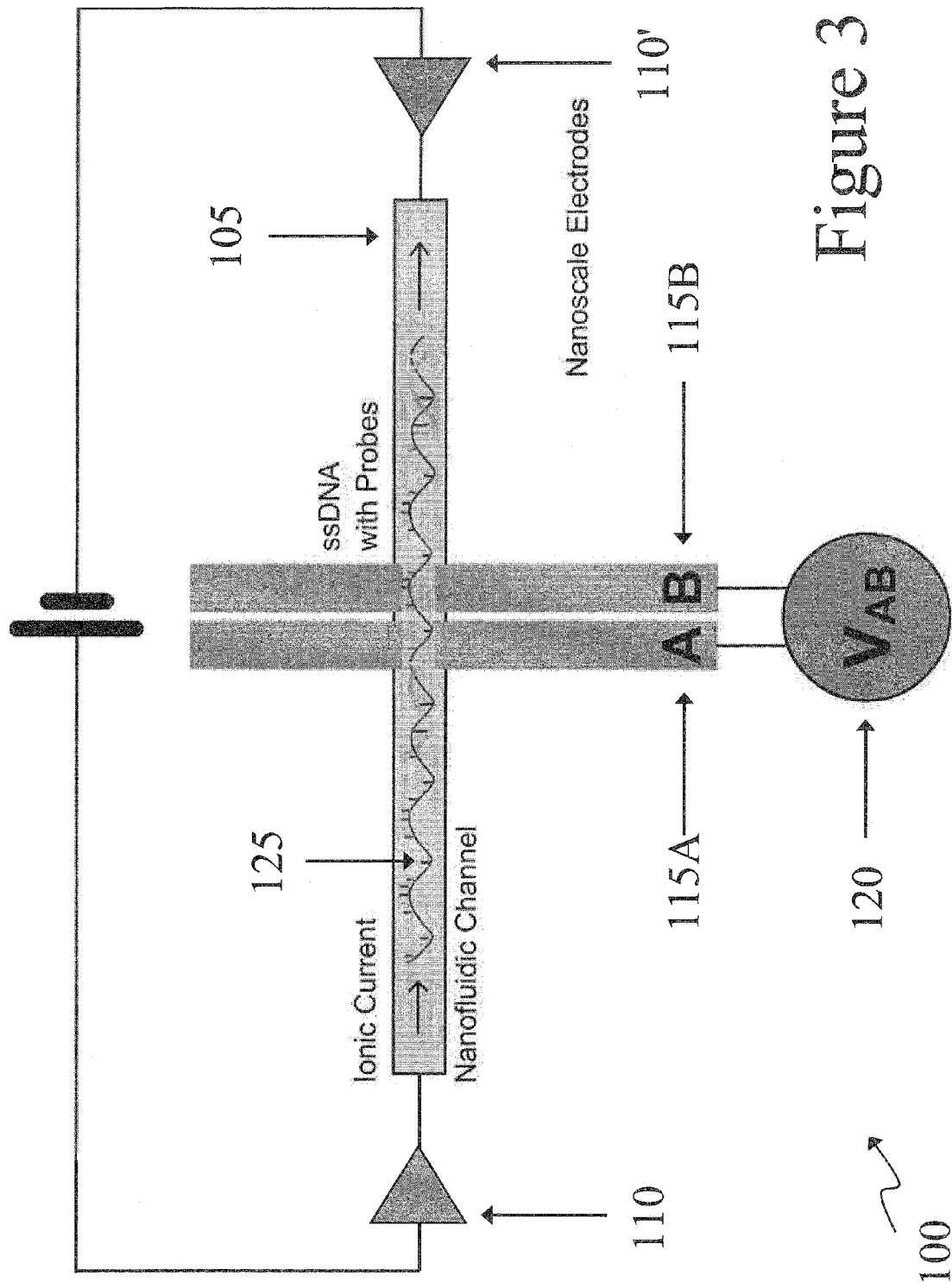
FIG. 3 is a schematic diagram illustrating a longitudinally displaced continuous transverse nanoscale electrode device configuration in accordance with another embodiment of the invention.
Figure 4:
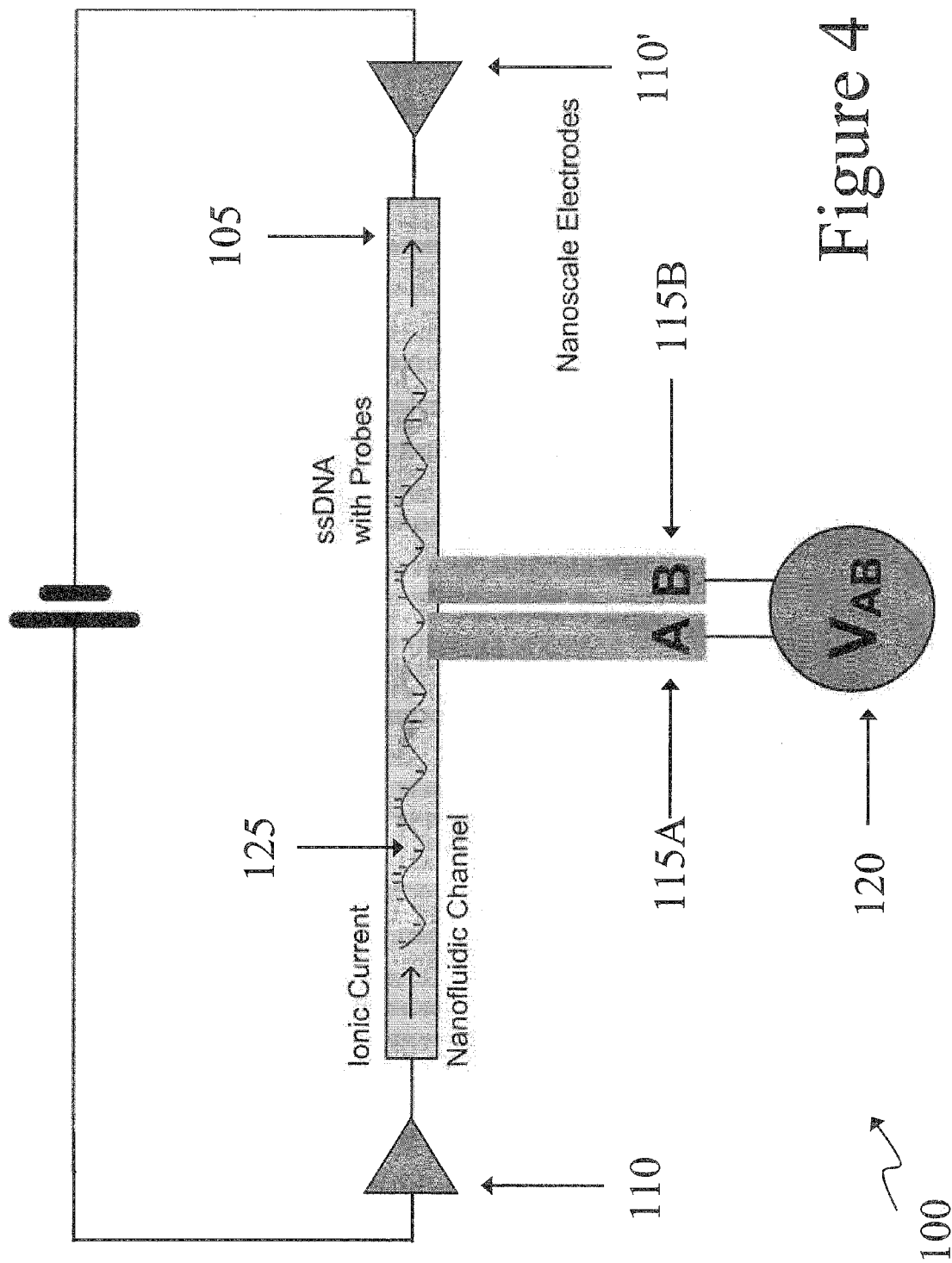
FIG. 4 is a schematic diagram illustrating a longitudinally displaced nano scale electrode device configuration with electrodes disposed on the same side of a nanochannel, in accordance with an embodiment of the invention.

By making the longitudinal distance, e.g., a length along the fluidic channel 105, between sensing electrodes 115A, 115B small, the device 100 retains high sensitivity for an analyte 125 passing therethrough. Each sensing electrode 115A, 115B in the pair may be disposed on opposite sides of the fluidic channel 105 as in FIG. 1, where tips of the sensing electrode 115A, 115B are in contact with the electrolytic solution are entirely or partially across from one another, or as in FIG. 2, in which the tips of the sensing electrodes 115A, 115B are not across from each other, but are rather longitudinally displaced with respect to one another by a selected distance. Alternatively, each sensing electrode 115A, 115B in a pair may cross the fluidic channel 105, as shown in FIG. 3. Referring to FIG. 4, in a third arrangement, two sensing electrodes 115A, 115B in a pair may be on the same side of the fluidic channel 105.

The devices 100 described herein may be formed by the fabrication of a trench to define a fluidic channel 105 having nanoscale dimensions, and the fabrication of nanoscale electrodes. A typical device 100 may also have a microscale fluidic structure for introduction of buffers and samples. Thus, the techniques described herein employing nanochannels are also applicable to devices including microchannels. Some or all of the structures may also be sealed with a cap in order to provide closed channels.

Fluidic channels may be formed in the substrate by, e.g., lithographic and etch steps. The substrate may be, e.g., a silicon-on-insulator wafer, with, for example, an (100) Si surface, a Si wafer, or a fused silica substrate. Lithography in the sub-100 nanometer (nm) regime may be performed by various techniques, including the following: electron beam lithography (EBL), nanoimprint lithography (NIL) or deep ultraviolet optical lithography (DUV OL). See Liang, X.; Morton, K. J.; Austin, R. H.; Chou, S. Y., Single sub-20 nm wide, centimeter-long nanofluidic channel fabricated by novel nanoimprint mold fabrication and direct imprinting, *Nano Lett.* 2007, 7, 3774-3780; Austin, M. D.; Ge, H.; Wu, W.; Li, M.; Yu, Z.; Wasserman, D.; Lyon, S. A.; Chou, S. Y., Fabrication of 5 nm line width and 14 nm pitch features by nanoimprint lithography, *App. Phys. Lett.* 2004, 84, 5299-5301; and Guo, J., Recent progress in nanoimprint technology and its applications, *J. Phys. D: Appl. Phys.* 2004, 37, R123-R141. Each of these references is incorporated herein by reference in its entirety. The current industry standard in micro and nanofabrication is optical lithography due to its low cost and high throughput. At present, optical lithography has been successfully used in the mass production of devices with critical dimensions as small as 32 nm. EBL and NIL are presently used extensively in academic research environments due to their versatility and capability of producing sub-10 nm features reproducibly. Any of these methods may be used to pattern the fluidic trenches described herein.

The removal of material for the formation of the fluidic trenches may be performed by, e.g., etching. Wet etching includes the immersion of the material in a solution capable of selective removal. Dry etching, i.e., reactive ion etching (RIE), involves the exposure of the sample to a charged plasma. For the resolution and control required of nanoscale fabrication, RIE is preferable due to its consistency, controllability, and efficiency. Microfluidic channels or reservoirs leading to the nanoscale channels may be etched using either wet or dry methods.

The resulting channels have preferred dimensions of width and depth ranging from 1 nm to 5 μm, more preferably 1 nm to 1 μm, and more preferably 10 nm to 100 nm. The channels may have a length selected from a range of, e.g., 1 micrometer (μm) to 10 centimeters (cm).

The size of the channel may be chosen with regard to the persistence length of the analyte. For example, a randomly coiled polymer (e.g., DNA) may be elongated when introduced into a confined space, such that when the confinement space becomes smaller the extent of elongation becomes greater. In some embodiments, it may be preferable to elongate the analyte to measure length or distance between probes. Depending on the cross-sectional size and the persistence length it may be useful to have the geometric mean of the width and depth of the channel be between 5% and 500% of the persistence length of the analyte. For example, for double-stranded DNA, under conditions where the persistence length is 50 nm, it may be preferable to have, e.g., a fluidic channel with a width and depth between 2.5 nm and 250 nm. In other embodiments, for more rigid polymers such as RecA coated DNA, under conditions where the persistence length is 950 nm, it may be preferable to have, e.g., a fluidic channel with a width and depth between 45 nm to 4.75 μm.

After the channels are formed, sensing electrodes are fabricated. Similar to etching and lithography, numerous metal deposition techniques suitable for fabrication of sensing electrodes exist in conventional microfabrication process flows. Each technique has positive and negative attributes and a list of the materials that may be deposited using that technique. The three primary techniques are: electron beam evaporation, thermal evaporation, and sputtering. The sensing electrodes have thicknesses ranging from 5 nm to 100 nm at the point where the sensing electrodes intersect the fluidic channels. The sensing electrodes may be wider and/or thicker in regions distal to the fluidic channels and approaching contact pads disposed at the perimeter of the device.

To complete the device, a cap layer may be introduced to prevent evaporation of liquid from the fluidic channel. The cap may be formed over just the nanoscale fluidic paths or over all of the fluidic channels. In the latter case, the cap structure preferably has holes or ports to allow for the introduction of fluid and samples into the fluidic paths. In another embodiment, the entire substrate, i.e., wafer, may be capped. The cap may be made of a glass plate such as borosilicate glass, phosphosilicate glass, quartz, fused silica, fused quartz, a silicon wafer or other suitable substrates. Various techniques are suitable for accomplishing this step including anodic bonding. In anodic bonding, an underlying silicon wafer and a glass substrate are pressed together and heated while a large electric field is applied across the joint. Anodic bonding has been demonstrated to form a strong bond between a silicon wafer and the capping substrate. Direct silicon bonding has been used to join two silicon wafers. The latter method involves pressing the two wafers together under water. Other methods use an adhesive layer, such as a photoresist, to bond the cap to the substrate.

An exemplary fabrication process for defining the proposed sensing element is as follows. A suitable substrate, such as a conventional (100) p-type silicon wafer, is thermally oxidized in a hydrated atmosphere to grow a thick (e.g., >1 μm) silicon-dioxide ($SiO_2$) layer. This $SiO_2$ layer may serve as insulation between subsequently formed adjacent metal sensing electrodes, and may also reduce overall device capacitance.

Using conventional high resolution optical lithography, the pattern of the fluidic channel may be transferred to a first photoresist masking layer. RIE with an anisotropic etch species, such as $Cl_2$, may be used to transfer the pattern into the $SiO_2$ layer. The preferred width and depth of the channel may be determined by the requirements for the device sensitivity. The smaller the volume of the channel between two sensing electrodes, the more sensitive the device is. Channel size, width, and depth, may also be determined by the size or behavior of the analyte. In one embodiment, the device described herein is used to detect strands of DNA. It may be desirable to fabricate the channel with dimensions that extend the DNA strand within the channel. For instance for double-stranded DNA, it has been found that the use of channels with dimensions of 100 nm or less are able to extend the biopolymer. See Tegenfeldt, J. O et al. *The dynamics of genomic-length DNA molecules in* 100-*nm channels*. Proc. Nat. Acad. Sci. USA, 2004, 101, 10979-10983, which is incorporated herein by reference in its entirety. Upon completion of the dry etch procedure, residual resist is removed and the substrate vigorously cleaned.

Following the etching of the fluidic channel, embedded metal sensing electrodes are fabricated. Conventional high resolution optical lithography may be used to transfer the metal electrode pattern to a second photoresist masking layer. RIE with an anisotropic etch species, such as $Cl_2$, will be used to transfer the pattern into the $SiO_2$ layer. Preferably the depth of these trenches exceeds or equals the depth of the fluidic channel. Upon completion of pattern transfer to the $SiO_2$ layer, a thin metal adhesion promotion layer may be deposited. A suitable layer is tantalum with a thickness of 30-50 Å, deposited via electron beam evaporation. Next, the sensing electrode material is deposited without exposing the substrate to atmosphere. A preferred metal for the bulk of the sensing electrodes is platinum, also deposited via electron beam evaporation. Other examples of suitable metals include gold, chrome, titanium, silver chloride, silver, and graphene. The thickness of the metal is dictated by the depth of the etched trenches, such that the resultant metal trace is approximately planar with a top surface of the $SiO_2$ layer. Upon completion of the metal deposition, the substrate is immersed in a photoresist solvent that will lift-off excess metal from the surface and the substrate is vigorously cleaned. Chemical-mechanical polishing (CMP) may be performed to remove excess metal extending over the $SiO_2$ top surface, thereby planarizing a top surface of the metal to be level with the $SiO_2$ top surface.

To complete the fabrication of the sensor, a cap layer is preferably adhered to the sensor surface to provide a leak-free seal, enabling fluidic conduction. Preferred cap materials include borosilicate glass, fused silica, fused quartz, quartz, or phosphosilicate glass. Holes may be created in the cap layer to provide access to fluidic inlet, fluidic outlet and metal sensing electrodes. A typical method for making holes in glass wafers is ultrasonic etching, which allows for highly controllable pattern transfer to glass substrates. Anodic bonding may then be used to bond the glass cap layer to the underlying substrate, e.g., silicon wafer. The anodic bonding of two layers provides a strong and leak-free seal.

An exemplary device with a pair of such nanoscale sensing electrodes 115A, 115B is illustrated in FIG. 1, i.e., electrodes A and B. Electric current is transferred in the form of ionic flow in an electrolyte solution confined in the fluidic channel 105, e.g., a nanochannel. The role of the electrolyte is to maintain a uniformly distributed electric field in the fluidic channel. Typical electrolyte solutions have been described in applications of electrophoresis to separations of DNA molecules. The most common electrolytes for electrophoretic separation of DNA are Tris boric acid EDTA (TBE) and tris acetate EDTA (TAE). See, e.g., Sambrook, J.; Russell, D. W. *Molecular Cloning: A Laboratory Manual* $3^{rd}$ ed. Cold Spring Harbor Press, 2001. However, any conductive medium may be used.

Operation of Device

During operation, a constant current is supplied by applying a potential to a pair of macroscopic electrodes, e.g., electromotive electrodes 110, 110' disposed at opposing ends of the fluidic channel 105 and in contact with the electrolytic solution. The electromotive electrodes are preferably in electrical communication with the wires leading to the ends of the fluidic channel 105 illustrated in FIGS. 1-4. A potential may be applied along the fluidic channel 105 to generate an electrophoretic force therein, such that the analyte 125 is translocated from a first end of the fluidic channel 105 to a second end of the fluidic channel. The electromotive electrodes may generate a constant or oscillating electrophoretic force in the fluidic channel 105 for translocation of an analyte 125 disposed therein. The voltage between the electromotive electrodes may be constant or it may be changed over the course of a measurement. For instance, it may be desirable to reduce the voltage once a DNA molecule has entered the fluidic channel 105 and before the DNA molecule has entered the volume between the sensing electrodes, in order to slow the passage of the DNA molecule through the volume between the sensing electrodes. Controlling the rate of passage of the DNA molecule through the volume between sensing electrodes 115A, 115B allows for more versatile detection of the DNA.

As an example of the placement of sensing electrodes, a width of 20 nm may be assumed for each of sensing electrodes A and B in FIG. 1. Electrode A may be shifted along the fluidic channel 105 relative to electrode B, by, e.g., 10 nm or 30 nm. Distances between sensing electrodes from 30 nm to 100 nm or from 30 nm to 500 nm, or from 30 nm to 5 μm can be incorporated into a single device. For analytes of sufficient length, distances up to e.g., 500 μm may be used, e.g., up to 300 μm, 200 μm, or 100 μm may be used. Although electrodes with any distance therebetween may be fabricated, since DNA is difficult to obtain at a length greater than 500 μm, any electrode distance that is greater than 500 μm would be superfluous, as long as the length of the DNA does not exceed 500 μm. The smaller displacement between electrodes A and B is an example of an embodiment in which there is overlap of the electrodes, even though they are displaced with respect to one another. In some embodiments, as shown in FIG. 2, there may be no overlap between sensing electrodes 115A, 115B.

The voltage across sensing electrodes 115A, 115B is proportional to the local impedance in the fluidic channel 105 between sensing electrodes 115A, 115B. The spacing of the electrodes is determined by several factors. The smaller the distance between electrodes in a sensing pair, all other factors being constant, the smaller the particle that can be detected by the sensing pair. However, fabrication limits may make it difficult to consistently place the electrodes in a pair at small distances. Thus, the selected distance is a trade-off between fabrication reproducibility and sensitivity of the device 100. The choice of separation distance and thus whether the electrodes are overlapping or non-overlapping depends on these constraints.

The resulting sensing electrode 115A, 115B arrangement provides a means to separate the current and voltage probes and can be used to employ 4-point sensing in a fluidic channel. In an embodiment, the macroscopic, electromotive electrodes 110, 110' at the ends of the fluidic channel 105 provide a current while the nanoscale sensing electrodes 115A, 115B disposed across the fluidic channel 105 are used to measure voltage. The voltage electrodes preferably have an output impedance higher than the impedance of the volume being measured.

The following calculations demonstrate the feasibility of this device concept. The fluidic channel may be subject to a constant electric field equal to the potential difference along the length of the channel divided by the length of the channel, i.e., 100 mV applied longitudinally to a 10 μm long fluidic channel results in a field of 100 mV/10 μm=10 mV/μm or 0.01 mV/nm. The potential difference between electrodes A and B separated by 10 nm is then the product of the distance between electrodes and the electric field or:

$$10 \text{ nm} \times 0.01 \text{ mV/nm} = 0.1 \text{ mV}.$$

Similarly, a potential difference of 0.3 mV exists between electrodes A and B when the spacing is 30 nm. Each of these potentials is readily detectable with conventional electronic measurement tools. When a DNA molecule or any other analyte passes between a pair of sensing electrodes, the impedance between the sensing electrodes changes due to a resistivity difference between the electrolyte and the molecule. The resulting transient change in the potential is measured, while maintaining a constant current.

For the example shown in FIG. 1, assuming a substantially constant velocity, the duration of each voltage pulse detected by the sensing electrodes 115A, 115B is proportional to the length of the DNA or other analyte 125 that passes between the two sensing electrodes. After determining the speed of the analyte 125 in the fluidic channel, the measured duration of the pulse may be used to calculate the distance the analyte 125 moved (velocity×time=distance) while passing through the volume between sensing electrodes, which would be equal to the analyte's 125 length.

It is important to note that by shifting one of the transverse electrodes along the fluidic channel 105 by a distance of 10-50 nm, and using a fluidic channel 105 with a diameter of about 10 nm, the volume separating the two sensing electrodes 115A, 115B may be viewed as having a sensitivity equivalent to that of a conventional solid-state nanopore.

In use, the voltage between a pair of sensing electrodes 115A, 115B, e.g., $V_{AB}$, may be sensed by a measurement tool 120, e.g., a voltmeter, configured to measure the potential difference between the sensing electrode 115A, 115B pair. In a preferred embodiment, the voltmeter 120 may be in electrical communication with each of the sensing electrodes 115A, 115B in the pair via metal contact pads connected to nanowires leading to the sensing electrodes.

Generally, an analyte 125 may be detected in the fluidic channel 105 as follows. The analyte, e.g., the biopolymer strand and probes, is transferred from a chamber into the fluidic channel in an electrolytic solution. Typically, an electrolyte may be added to the fluidic channel by a pipette, a syringe, or a pump. An analyte sample size may be as small as practically possible, as the device allows the detection of single molecules. The fluid may wet the fluidic channels by capillary action. Analyte may be introduced into the microscale areas either with the original electrolyte or after by pumping in a new solution. An analyte, such as DNA, which may be hybridized to one or more probes, may be drawn into the fluidics channel by the potential. For small analytes, one could use diffusion, fluid flow, or a potential.

The fluidic channel may have a width that is no smaller than approximately the same width as the analyte, and may be sufficiently large such that large molecules bound to the analyte may pass through the fluidic channel. For example, the width of the fluidic channel may be selected from a range of 1 nm to 200 nm. The fluidic channel may be sufficiently deep to allow large molecules bound to the analyte to pass through and yet shallow enough to be approximately the same size as the analyte. The fluidic channel depth may be, e.g., selected from a range of 1 nm to 200 nm. The length of the fluidic channel may be selected such that the entire analyte is contained in the fluidic channel.

In an embodiment, the sensing electrodes and fluidic channel may be preferably arranged such that the entire analyte enters the fluidic channel before it enters the volume between sensing electrodes. This configuration provides an advantage of reducing the effect of the analyte on the conductance of the fluidic channel. For instance, if one is beginning to measure the change in potential of a volume between sensing electrodes while the conductance of the whole fluidic channel is changing due to more analyte entering the fluidic channel, the analysis becomes more complex In a preferred embodiment, the analyte may be contained completely in the channel when it exits the volume between sensing electrodes. Thus, the length of the fluidic channel preferably has a minimum length that is approximately three times the length of the analyte (assuming that the volume between sensing electrodes is only as long as the analyte, which is a minimal requirement but not optimal). The length of a 1 kb piece of DNA is about 330 nm, so a length of the fluidic channel is preferably at least 1 μm in length. The longest piece of DNA suitable for analysis with the described methods may be 10 megabases (Mb), which corresponds to a preferred fluidic channel of at least 10 mm. More preferably, the length of a fluidic channel is ten times the length of the analyte, and thus a more preferred upper limit for a channel length is 100 mm (10 cm) Thus, the fluidic channel length is preferably selected from a range from 1 μm to 10 cm. Longer and shorter fluidic channel lengths are also possible.

In some embodiments, the structure of the fluidic channel may facilitate entry of the analyte into the channel, e.g., the fluidic channel may comprise a series of posts (e.g., U.S. Pat. No. 7,217,562, which is incorporated by reference in its entirety) and/or a funnel shape.

The analyte is translocated through the fluidic channel by a current that is supplied by applying a potential to the two electromotive electrodes disposed at opposing ends of the fluidic channel and in contact with the electrolytic solution. The electromotive electrodes may generate a constant or oscillating electrophoretic force in the fluidic channel for translocation of an analyte disposed therein. The voltage between the macroscopic electrodes may be constant or it may be changed over the course of a measurement. For example, the voltage may be reduced once a DNA molecule has entered the fluidic channel and before the DNA molecule has entered the volume between the sensing electrodes, to slow the passage of the DNA molecule through the volume between sensing electrodes.

A voltage signal reflecting a change in potential between the pair of sensing electrodes may be monitored. As the analyte moves through a volume between the sensing electrodes, the voltage signal changes. The signal may be elevated or depressed for a period of time that reflects the length of the analyte, e.g., a probe-target complex, or the length of the intervening regions without probes. A typical analyte is non-conductive and will impede the flow of ions in the electrolyte. Therefore, the potential—and voltage signal—typically increase as the analyte flows through the volume between sensing electrodes. In some embodiments, e.g., a low salt electrolyte and a charge-carrying analyte, the potential and voltage signal may decrease as the analyte flows through the volume between sensing electrodes. The voltage signal further changes when the portion of the analyte containing the hybridized probe moves through the volume between the sensing electrodes.

Determination of Analyte Length and Probe Location

In an embodiment, a method for detecting the relative position of probes hybridized to a biopolymer and/or the length of the biopolymer. Nanopores may be used as detectors to determine the distance between hybridization sites as described in U.S. Patent Publication No. 2007/0190542 A1, which is incorporated herein by reference in its entirety. The construction of a nanochannel device incorporating voltage detectors is described herein. In both the nanopore and the fluidic channel (e.g., a nanochannel), the distance between hybridization sites on the target biopolymer may be inferred from the time between the detection of a first hybridization position and a subsequent hybridization position as the biopolymer moves through the nanopore or fluidic channel. The technology disclosed herein allows the determination of biopolymer length and distances between hybridization positions.

In particular, as used herein, a "probe" means any molecule or assembly of molecules capable of sequence-specific covalent or non-covalent binding to a target molecule. A probe may be, but is not limited to, a DNA sequence, an RNA sequence, antibodies or antibody fragments. The terms "nucleotide" and "base" are used interchangeably and mean a molecule consisting of a phosphate group, a sugar and one of five nitrogen-containing bases that can make up DNA or RNA polynucleotide chains or strands. For DNA, the nitrogen-containing bases include cytosine (C), adenine (A), guanine (G) and thymine (T) and the sugar is a 2-deoxyribose. For RNA, a the deoxyribose sugar is replaced by a ribose sugar instead of deoxyribose and uracil bases (U) instead of thymine bases (T).

A DNA probe "library" is a collection of DNA probes of a fixed length which includes a large number of, or possibly all, possible sequence permutations. A plurality of probes may be made up of multiple copies of the same probe with the same sequence selectivity or be made up of two or more probes with different sequence selectivity. A "probe map" means a data set containing information related to the sites along a target sequence at which a probe preferentially binds. A partially hybridized biomolecule is created when the entire length of a sequence selective probe binds to a portion of the length of the target biomolecule. The data set may include absolute positional information referenced to a known sequence, relative information related to distances between binding sites, or both. The data set may be stored in computer media. Further details of the characteristics of probe and spectrum maps may be found in U.S. Patent Publication No. 2009-0099786 A1, which is incorporated herein by reference in its entirety.

A "target," i.e., the analyte, is a biopolymer, of which length, identity or sequence information is to be determined using embodiments of the present invention. The analyte may be a biopolymer, such as a deoxyribonucleic acid, a ribonucleic acid, proteins, or a polypeptide. The target DNA may be single- or double-stranded. In some embodiments, the analyte is a biopolymer to which probes have been hybridized.

DNA is the fundamental molecule containing all of the genomic information required in living processes. RNA molecules are formed as complementary copies of DNA strands in a process called transcription. Proteins are then formed from amino acids based on the RNA patterns in a process called translation. The common relation that can be found in each of these molecules is that they are all constructed using a small group of building blocks, such as bases or amino acids, that are strung together in various sequences based on the end purpose that the resulting biopolymer will ultimately serve.

Figure 5:
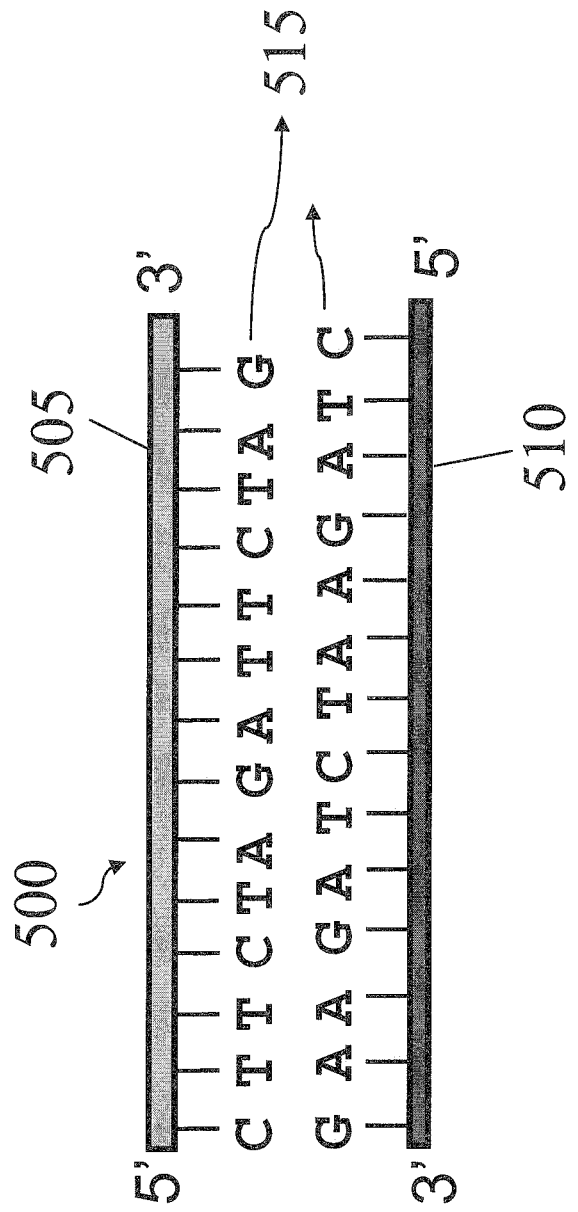
FIG. 5 is a schematic depiction of a DNA molecule (SEQ ID NO: 1)
Figure 6:
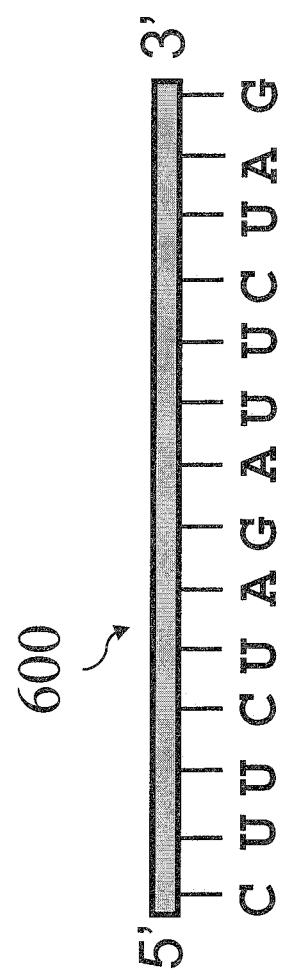
FIG. 6 is a schematic depiction of an RNA molecule (SEQ ID NO: 2)

Analytes may be prepared for analysis, e.g., as disclosed in U.S. Patent Publication No. 2007/0190542, which is incorporated herein by reference in its entirety. Referring to FIG. 5, a DNA molecule 500 is schematically depicted and can be seen to be structured in two strands 505, 510 positioned in anti-parallel relation to one another. Each of the two opposing strands 505, 510 is sequentially formed from repeating groups of nucleotides 515 where each nucleotide 515 consists of a phosphate group, 2-deoxyribose sugar and one of four nitrogen-containing bases. The nitrogen-containing bases include cytosine (C), adenine (A), guanine (G) and thymine (T). DNA strands 505 are read in a particular direction, from the so called the 5' or "five prime" end to the so called the 3' or "three prime" end. Similarly, RNA molecules 600, as schematically depicted in FIG. 6 are polynucleotide chains, which differ from those of DNA 500 by having ribose sugar instead of deoxyribose and uracil bases (U) instead of thymine bases (T).

Traditionally, in determining the particular arrangement of the bases 515 in these organic molecules and thereby the sequence of the molecule, a process called hybridization is utilized. The hybridization process is the coming together, or binding, of two genetic sequences with one another. This process is a predictable process because the bases 515 in the molecules do not share an equal affinity for one another. T (or U) bases favor binding with A bases while C bases favor binding with G bases. This binding is mediated by the hydrogen bonds that exist between the opposing base pairs. For example, between an A base and a T (or U) base, there are two hydrogen bonds, while between a C base and a G base, there are three hydrogen bonds.

Figure 7:
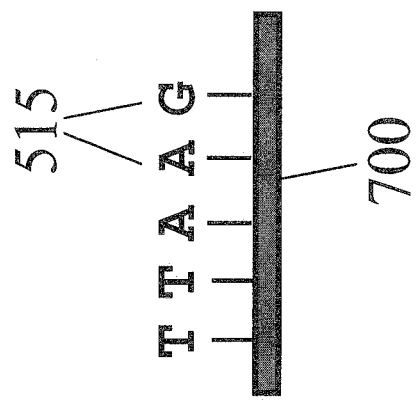
FIG. 7 is a schematic depiction of a hybridizing oligonucleotide (or probe)

The principal tool that is used then to determine and identify the sequence of these bases 515 in the molecule of interest is a hybridizing oligonucleotide commonly called a probe 700. As FIG. 7 illustrates, a DNA probe 700 is a DNA sequence having a known length and sequence composition. Probes 700 may be of any length dependent on the number of bases 515 that they include. For example a probe 700 that includes six bases 515 is referred to as a six-mer wherein each of the six bases 515 in the probe 700 may be any one of the known four natural base types A, T(U), C or G and alternately may include non-natural bases. In this regard the total number of probes 700 in a library is dependent on the number of bases 515 contained within each probe 700 and is determined by the formula $4^n$ (four raised to the n power) where n is equal to the total number of bases 515 in each probe 700. Accordingly, the general expression for the size of the probe library is expressed as $4^n$ n-mer probes 700. For the purpose of illustration, in the context of a six-mer probe the total number of possible unique, identifiable probe combinations includes $4^6$ (four raised to the sixth power) or 4096 unique six-mer probes 700. It should be further noted that the inclusion of non-natural bases allows the creation of probes that have spaces or wildcards therein in a manner that expands the versatility of the library's range of probe recognition. Probes that include universal bases organized into patterns with natural bases may also be used, for example those described in U.S. Pat. Nos. 7,071,324, 7,034,143, and 6,689,563, each of which are incorporated herein by reference in their entireties.

When a target biomolecule, such as single-stranded DNA, is incubated with a sequence selective probe under appropriate conditions, the probe hybridizes or binds to the biomolecule at specific sites. The determination of the relative location of the hybridization sites is useful for constructing maps of the target biomolecule, and for identifying the target molecule.

Figure 8:
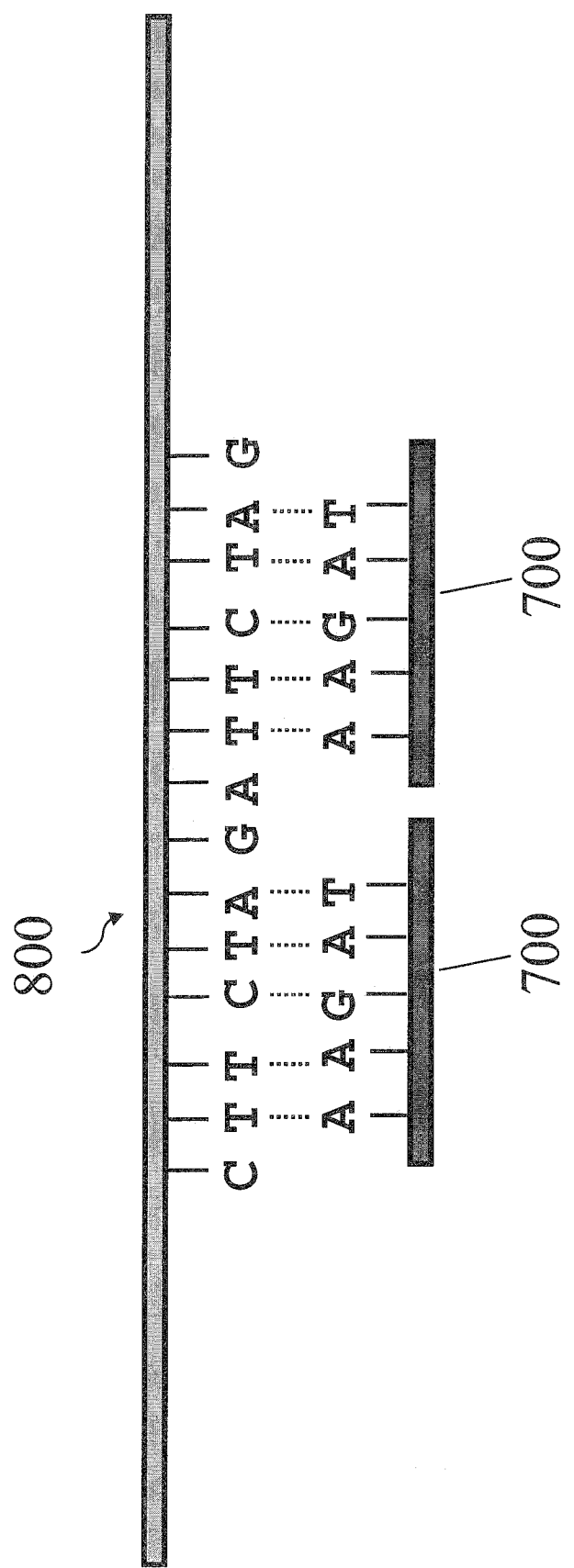
FIG. 8 is a schematic depiction of a single strand DNA molecule (SEO ID NO: 1) hybridized with a probe.

When the biopolymer to be analyzed is a double-stranded DNA 500, the process of hybridization using probes 700 as depicted in FIG. 8 first requires that the biopolymer strand be prepared in a process referred to as denaturing. Denaturing is a process that is usually accomplished through the application of heat or chemicals, wherein the hydrogen bonds between the two strands of the original double-stranded DNA are broken, leaving a single strand of DNA whose bases are available for hydrogen bonding. After the biopolymer 800 has been denatured, a single-stranded probe 700 is introduced to the biopolymer 800 to locate portions of the biopolymer 800 that have a base sequence that is complimentary to the sequence that is found in the probe 700. In order to hybridize the biopolymer 800 with the probe 700, the denatured biopolymer 800 and a plurality of the probes 700 having a known sequence are both introduced to a solution. The solution is preferably an ionic solution and more preferably is a salt containing solution. The mixture is agitated to encourage the probes 700 to bind to the biopolymer 800 strand along portions thereof that have a matched complementary sequence. Once the biopolymer strand 800 and probes 700 have been hybridized, the strand 800 is introduced to one of the chambers of a sequencing arrangement. It should also be appreciated to one skilled in the art that while the hybridization may be accomplished before placing the biopolymer strand 800 into the chamber, it is also possible that the hybridization may be carried out in one of these chambers as well. In this case, after the denatured biopolymer has been added to the cis chamber, a drop of buffer solution containing probes 700 with a known sequence are also added to the cis chamber and allowed to hybridize with the biopolymer 800 before the hybridized biopolymer is translocated.

As a specific example of analyte preparation, a nucleotide sample, such as DNA or RNA, may be heated to a denaturing temperature, typically greater than 90° C. for DNA and typically between 60-70° C. for RNA, in the presence of a selection of probes and in a buffer of 50 mM potassium chloride and 10 mM Tris-HCl (pH 8.3). The hybridization may be accomplished in the cis chamber or before placing the analyte in the chamber. The mixture of nucleotide strand and probes are then cooled to allow for primer binding, with the temperature dependent upon the length and composition of the probe. For example, a 6-nucleotide probe would be cooled to room temperature or lower. The nucleotide strand and probe may be allowed to anneal at the low temperature for up to 5 minutes before being passed through a fluidic channel for analysis. The exact temperatures may be easily determined by one of skill in the art without undue experimentation.

Figure 9:
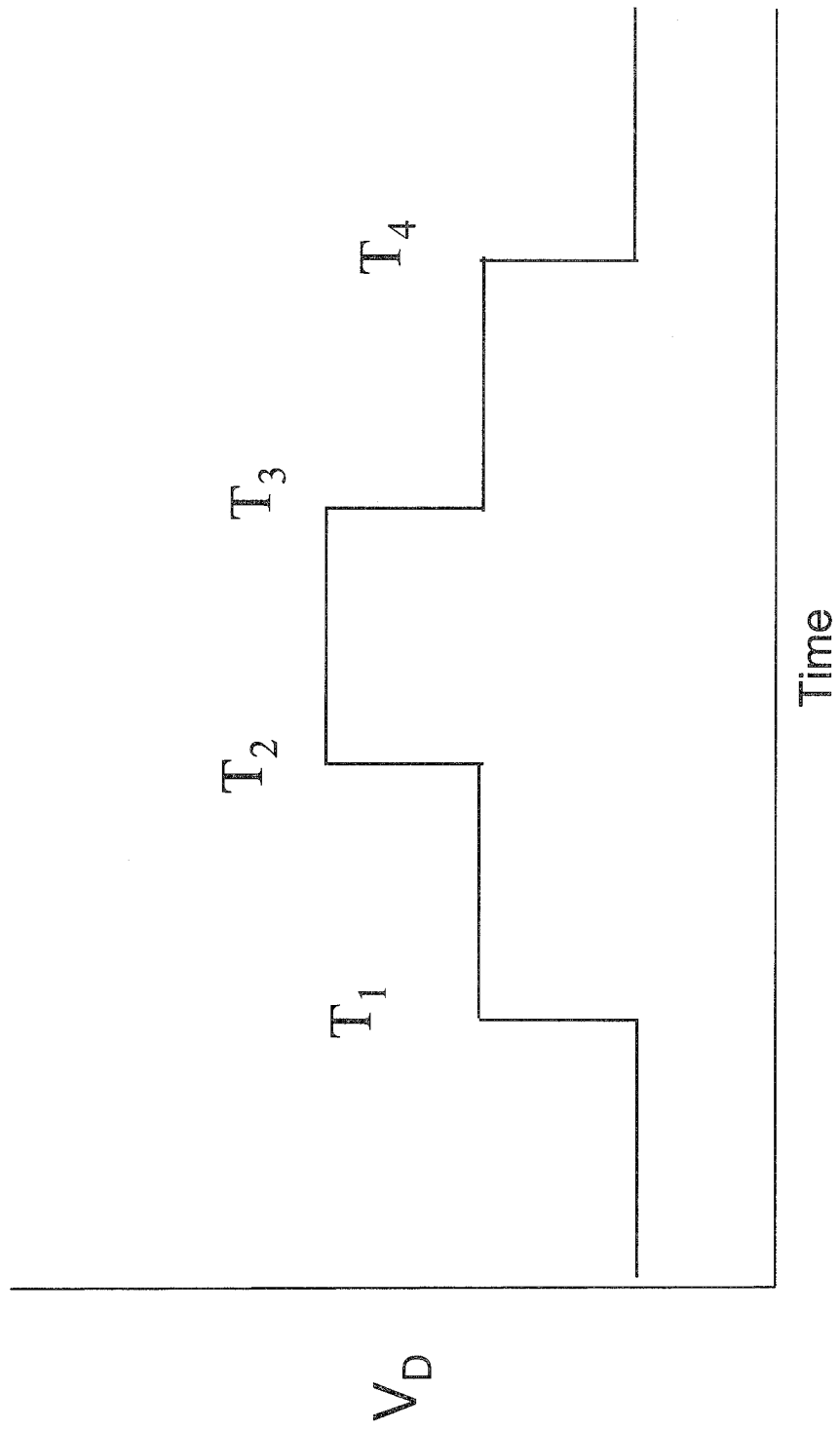
FIG. 9 is a graph of an exemplary voltage signal determined in accordance with an embodiment of the invention.

Referring to FIG. 1, in some embodiments, electrical signals corresponding to the volume between sensing electrodes 115A, 115B are detected by the sensing electrodes 115A, 115B as an analyte 125, e.g., a biopolymer, is disposed in the fluidic channel. As the biopolymer enters the volume between sensing electrodes, a change in the electrical signal is recorded. Referring to FIG. 10, the electrical signal increases linearly at time point $T_1$ as the analyte enters the volume between sensing electrodes. When the volume between sensing electrodes is completely filled, the signal stays essentially constant. When the analyte leaves the volume between sensing electrodes, the signal returns to baseline at time point $T_4$. The sensing electrodes are configured for connection to a measurement tool for capturing the electrical signals corresponding to the volume between sensing electrodes, e.g., a voltmeter. Electrical signals captured by the measurement tool may be recorded as a function of time by a data collection device, e.g., a Stanford Research Instruments SIM970 voltmeter. A time interval between voltage signal changes may be recorded. The duration of the change in the voltage signal over baseline may indicate a presence of an analyte. Another increase over that, as shown in FIG. 9 between time points $T_2$ and $T_3$, may indicate the presence of a probe hybridized with the analyte. The electrical signal may have fluctuations from noise and from the fact that a long analyte, such as DNA, typically has small bends in it. When a section having a bend enters the volume between sensing electrodes, the electrical signal may increase slightly, and then may decrease slightly when the bend exits the volume between sensing electrodes. Calibration of the electrical signals, therefore, may be needed to determine length. To determine the length of the analyte, one may calibrate the system with one or more standards, e.g., biopolymers of known, varying lengths, to determine the pulse duration and speed of each biopolymer length. Under consistent voltage and electrolyte conditions, this data may be used to create a standard curve for correlating the pulse duration of the analyte with its length.

Similarly, the duration of a change in the voltage signal may be used to determine the location of hybridization of a first plurality of probes and a distance between two probes on the biopolymer. The detected electrical signal corresponding to volume between sensing electrodes of the fluidic channel may be detected by using the sensing electrodes. As shown in FIG. 9 at time point $T_1$, the electrical signal may initially change when the biopolymer moves through a volume between sensing electrodes and further change, at $T_2$, when a portion of the biopolymer including a hybridized probe moves through the volume between sensing electrodes. The detected electrical signals may indicate the locations of the hybridized probes along the biopolymer. Changes and duration of changes in electrical signals may be analyzed to determine the location of probes with known sequence specificity along the length of the biopolymer. Distances between probes may be based upon the duration between voltage spikes representing hybridized probes just as the duration of spike is used to determine biopolymer length. For example, one may consider the average of the voltage signals when determining the distance between hybridized probes. Outliers may be excluded if they deviate greatly from other measurements taken of the same molecule. This analysis may be done either visually or with the assistance of a computer program that executes the analysis described herein.

The calculation of distances between probes may be used to determine the sequence of a biopolymer as follows. An analyte may be prepared by hybridizing a first plurality of probes with a known sequence with the biopolymer such that the first plurality of probes attaches to portions of the biomolecule to produce a partially hybridized biomolecule. The analyte may be disposed in a fluidic channel. A potential may be applied along the fluidic channel to generate an electrophoretic force therein such that the analyte is translocated from a one end of the fluidic channel to another end of the fluidic channel. Changes in the voltage are used to detect the hybridized probe as described above.

At least a portion of the sequence of the biopolymer may be determined by detecting the hybridization of the first plurality of probes. Its location on the biopolymer may be determined by using a distance from the end of the biopolymer to a probe's site of hybridization or the distance from a probe site of hybridization to another probe site of hybridization. A computer algorithm may be used to process the electrical signals to help determine the sequence of the biopolymer.

In some embodiments, a second plurality of probes having specificity for recognition sites on the target molecule may be hybridized with the biopolymer, either subsequently or in parallel to the first probe, to form individual pluralities of hybridization and the detecting, analyzing, and determining steps may be repeated with the subsequent plurality of probes.

The biopolymer may include a double-stranded biopolymer target molecule. The analyte may be prepared by contacting the biopolymer, i.e., the target molecule, with a first probe having a first probe specificity for recognition sites of the target molecule to form a first plurality of local ternary complexes.

The electrical signals may be used to detect and record complexed and uncomplexed regions of the biopolymer to create a first probe map of the first plurality of probes and subsequent probe maps for each subsequent plurality of probes, the first probe map and subsequent probe maps each including information about the relative positions of the hybridized first and each of the subsequent plurality of probes. Each probe map may include a series of numbers that indicate the distances between probes. The numbers may indicate distance in terms of base pairs or distance in terms of nanometers. A candidate sequence for at least a portion of the biopolymer may be determined by ordering at least two probe sequences using positional information and/or a combination of overlapping probe binding sequences and positional information.

The first and second probe maps may include information about an error of the positional information for each probe. For example, each indicated distance may have an associated standard deviation, e.g., 100 nm±10 nm. Further, a candidate sequence may be determined by ordering at least two probe sequences using at least one of (i) positional information and parameters relating to the error in positional information or (ii) a combination of overlapping sequences of the probe molecules and positional information and error in positional information.

The sequencing of biopolymers by hybridization of probes to form ternary complexes is further discussed in patent application U.S. Ser. No. 12/243,451 which is incorporated herein by reference in its entirety. Additional background information about detection/sequencing may be found in Gracheva, M. E.; Xiong, A.; Aksimentiev, A.; Schulten, K.; Timp, G, Leburton, J.-P. Simulation of the electric response of DNA translocation through a semiconductor nanopore-capacitor, *Nanotechnology* 2006, 17, 622-633; and Zwolak, M.; Di Ventra, M. Physical approaches to DNA sequencing and detection, *Rev. Mod. Phy.* 2008, 80, 141-165, each of which is incorporated herein by reference in its entirety.

Example of Length Determination

A sensing device composed of two microfluidic chambers, one or more fluidic channels connecting the two microfluidic chambers, and a pair of sensing electrodes disposed along the length of each fluidic channel, is filled with an ionic fluid. Typically, the fluid may be water that contains salt.

Multiple copies of a fragment of DNA of unknown length may be introduced into one of the microfluidic chambers that is connected to the fluidic channel that contains a pair of sensing electrodes. Macroscopic electrodes are used to electrophorese the DNA strands from the microfluidic chamber into one or more fluidic channels. As the DNA enters the fluidic channel, it assumes a linear conformation. The degree to which it is linearized depends on a number of factors. Some of those factors are, e.g., the persistence length of the DNA strand, the temperature, the ionic conditions, and the width and depth of the fluidic channel.

The potential applied by the electromotive electrodes causes the DNA strand to move down the length of the fluidic channel. As the fragment moves down the fluidic channel it passes through the volume between sensing electrodes. When the leading edge of the DNA enters a volume between sensing electrodes, a change in some electrical characteristic such as cross channel current or potential between two sensing electrodes may be recorded. The recorded signal is composed of a time stamp and an indication of change in potential or other electrical property. The value of the electrical property may also be recorded. The value may be subtracted from the background signal or may be an absolute value. A table may be generated by a computer that lists all responses occurring in the volume between sensing electrodes and the time stamp for each response. A computer program may subsequently determine the duration of the signal. As the trailing edge of the DNA strand exits the volume between sensing electrodes, the electrical response typically returns to the value which was observed before the DNA entered the volume. The magnitude of the electrical response depends on the experimental set-up; preferably, the electrical response is equal to at least 3 times the magnitude of the root mean square noise for the system.

A calibrated standard curve may be applied to the measured length in order to calculate the true length of the analyte. For example, the device may be calibrated with a series of DNA fragments of known length that are electrophoresed through the fluidic channel under the same conditions, e.g., ionic strength, temperature, pH as the analyte. The fragments preferably span enough different lengths to cover the range that may be used in the experiment to measure the length of the unknown fragment.

Example of DNA Sequencing

A target DNA strand of known or unknown sequence may be denatured. Denaturation of the duplex DNA is typically accomplished through the application of heat or chemicals, such that the hydrogen bonds between paired strands are broken. The denatured DNA sample is incubated with a probe of known sequence and base length or divided for incubation with multiple probes, each with their own specific recognitions sequences on the target DNA. In order to hybridize the probe or probes to their recognition sequence or sequences, the conditions for the incubation are chosen such that the probe or probes bind to the known specific recognition site in preference to other sites or mismatch sites. The conditions are also chosen so that more of the probe binding sites on the denatured DNA strands are bound to a probe than unbound. The solution may be a buffered ionic solution. The solution may be agitated to facilitate binding of the probes. The temperature of the solution may be varied during the course of the incubation. For instance, the temperature of the incubation may be slowly cooled over the course of the hybridization.

Once the denatured target DNA has been hybridized with a probe or probes, the sample is introduced into a microfluidic chamber at one end of the fluidic channel device. The fluidic channel device is filled with an ionic solution, e.g., a salt solution. The solution may also be buffered. The excess probe or probes may be removed prior to the introduction of the sample into the microfluidic chamber. Gel filtration is one method for removing short probes from a longer strand of DNA. Alternatively, other commercially available purification methods are available. Once the target DNA strand with hybridized probes has been introduced into a microfluidic chamber, a potential is applied via electromotive electrodes to drive the DNA from the microfluidic chamber into one or more fluidic channels.

The target DNA, upon entering the fluidic channel, typically assumes a linearized conformation. The narrower the fluidic channel, the more linearized the DNA is forced to become. The voltage applied to the macroscopic electromotive electrodes electrophoretically drives the DNA down the fluidic channel. As the DNA and hybridized probes move down the fluidic channel they enter the volume between sensing electrodes in the fluidic channel.

In the absence of DNA, the volume between sensing electrodes may contain only the ionic solution and have a baseline potential difference measured between the two sensing electrodes. As DNA enters the volume between sensing electrodes, the potential measured between the two sensing electrodes changes because the DNA has a conductivity different from that of the ionic solution. When DNA enters the volume between sensing electrodes, the conductivity of the channel between the two sensing electrodes is typically reduced with respect to the conductivity when only ionic fluid is present between the sensing electrodes. When a portion of the DNA that also has a probe hybridized thereto enters the volume between sensing electrodes, the potential changes further.

As the molecule passes between sensing electrodes, the monitored voltage varies by a detectable and measurable amount. The electrodes detect and record this variation in voltage as a function of time. These variations in voltage are the result of the relative diameter of the molecule that is passing between sensing electrodes at any given time. For example, the portions of the biomolecule that have probes bound thereto are twice the diameter of the portions of the biomolecule that have not been hybridized and therefore lack probes.

This relative increase in volume of the biomolecule passing between sensing electrodes causes a temporary increase in resistance between sensing electrodes resulting in a measurable voltage variation. As the portions of the biomolecule that include probes pass between sensing electrodes, the current is further impeded, forming a relative spike in the recorded voltage during passage of the bound portion, which decreases again after the hybridized portion has passed. The sensing electrodes detect and reflect these variations in the monitored current. Further, the measurements of the voltage variations are measured and recorded as a function of time. As a result, the periodic interruptions or variations in resistance indicate where, as a function of relative or absolute position, the known probe sequence has attached to the biomolecule.

When the DNA or a probe on the target DNA enters a fluidic channel, an electrical signal is recorded. The electrical signal is composed of a time stamp and the value of the changed electrical property. The electrical property value may be subtracted from the background signal or may be an absolute value. A table may be generated by a computer that lists all responses occurring between sensing electrodes and the time stamp for each response. A computer program may subsequently determine the length of the biopolymer and the location of the hybridized probes on the biopolymer. The location of the probe on the biopolymer may be determined in terms of nanometers, base pairs or percentage of total biopolymer length.

The probe's location on the biopolymer can be determined according to its distance from the end of the biopolymer. This may be done through a determination of a total length of the biopolymer using a calibrated standard. The duration of the biopolymer signal may be compared to a calibrated standard curve in order to calculate the true length of the analyte. For example, the device may be calibrated with a series of DNA fragments of known length that are electrophoresed through the fluidic channel under the same conditions as the analyte, e.g., ionic strength, temperature, pH. The fragments preferably span enough different lengths to calibrate the sensing electrodes to measure the length of the unknown fragment.

More of the sequence can be determined through subsequent or parallel hybridization with a second plurality of probes and the detecting, analyzing, and determining steps may be repeated with the subsequent plurality of probes. The designs described herein merge nanopore and fluidic channel technologies and decouple the driving electrophoretic force from the detected signal. By using voltage sensing and by fabricating voltage amplifiers directly on the substrate where the sensing electrodes are placed, the device may operate at higher frequencies than has been possible with previous geometries.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A device for voltage sensing of analytes, the device comprising:

a fluidic channel defined by a trench in a substrate;

a pair of sensing electrodes disposed in the channel for sensing voltage therein, the pair of sensing electrodes comprising a first and a second sensing electrode disposed at two discrete laterally offset locations along a length of the fluidic channel, the pair of sensing electrodes being connected to a voltmeter for measuring a voltage sensed by the pair of sensing electrodes, and the pair of sensing electrodes not being connected to a voltage source; and a pair of electromotive electrodes disposed at a first end and a second end of the fluidic channel for applying a potential along the fluidic channel, wherein the fluidic channel comprises a nanochannel or a microchannel.

2. The device of claim 1, wherein the substrate comprises a material selected from the group consisting of silicon, silicon dioxide, fused silica, and gallium arsenide.

3. The device of claim 1, wherein each of the sensing and electromotive pairs of electrodes comprises a material selected from the group consisting of platinum, gold, chrome, titanium, silver chloride, silver, and graphene.

4. The device of claim 1, wherein the first sensing electrode is disposed on a first side of the fluidic channel and the second sensing electrode is disposed on an opposing side of the fluidic channel.

5. The device of claim 1, wherein each of the first and second sensing electrodes is disposed on a first side of the fluidic channel.

6. The device of claim 1, wherein each of the first and second sensing electrodes transverses the fluidic channel.

7. The device of claim 1, wherein the first sensing electrode transverses the fluidic channel and the second sensing electrode is disposed on a side of the fluidic channel.

8. The device of claim 1, wherein the electromotive pair of electrodes comprises macroscopic electrodes for generating a constant, changing, or oscillating electrophoretic force in the fluidic channel for translocation of an analyte disposed therein.

9. The device of claim 1, further comprising a plurality of fluidic channels.

10. The device of claim 1, further comprising a voltage amplifier disposed on the substrate.

11. The device of claim 1, wherein the fluidic channel has a width selected from a range of 1 nm to 5 μm.

12. The device of claim 1, wherein the fluidic channel has a depth selected from a range of 1 nm to 5 μm.

13. The device of claim 1, wherein the fluidic channel has a length selected from a range of 1 μm to 10 cm.

14. A method for detecting an analyte, the method comprising the steps of:
disposing the analyte in a fluidic channel defined by a trench in a substrate;
applying a potential along the fluidic channel;
translocating the analyte from a first end of the fluidic channel to a second end of the fluidic channel; and
measuring a voltage signal between a pair of sensing electrodes disposed in the fluidic channel for sensing voltage therein as the analyte moves past the pair of sensing electrodes, the pair of sensing electrodes comprising a first and a second electrode disposed at two discrete laterally offset locations along a length of the fluidic channel, the pair of sensing electrodes being connected to a voltmeter for measuring a voltage sensed by the pair of sensing electrodes and the pair of sensing electrodes not being connected to a voltage source,
wherein the fluidic channel comprises a nanochannel or a microchannel.

15. The method of claim 14, wherein applying a potential along the fluidic channel comprises generating an electrophoretic force therein.

16. The method of claim 14, wherein translocating the analyte comprises using a pressure differential.

17. The method of claim 14, wherein translocating the analyte comprises using a chemical gradient.

18. The method of claim 14, wherein the analyte comprises a biopolymer selected from the group consisting of deoxyribonucleic acids, ribonucleic acids, and polypeptides.

19. The method of claim 18, wherein the biopolymer comprises a single-stranded molecule.

20. The method of claim 14, wherein the analyte comprises a biopolymer having at least one probe attached thereto.

21. The method of claim 20, wherein the voltage signal changes when the biopolymer moves through a volume between the sensing electrodes and further changes when the portion of the biopolymer containing the probe moves through the volume between the sensing electrodes.

22. The method of claim 21, further comprising recording a time between voltage signal changes.

23. The method of claim 22, wherein a duration of a change in the voltage signal indicates a presence of a probe, further comprising using the voltage signal to determine a distance between two probes on the biopolymer.

24. The method of claim 14, further comprising using a duration of a change in the voltage signal to determine a length of the analyte.

25. A method for determining a sequence of a biopolymer, the method comprising:
disposing an analyte in a fluidic channel defined by a trench in a substrate;
applying a potential along the fluidic channel;
translocating the analyte from a first end of the fluidic channel to a second end of the fluidic channel; and
measuring an electrical signal between a pair of sensing electrodes disposed in the fluidic channel for sensing an electrical property therein as the analyte moves past the pair of sensing electrodes, the electrical property corresponding to locations along the biopolymer, the pair of sensing electrodes comprising a first and a second electrode disposed at two discrete laterally offset locations along a length of the fluidic channel, the pair of sensing electrodes being connected to voltmeter for measuring the electrical property sensed by the pair of sensing electrodes, and the pair of sensing electrodes not being connected to a voltage source,
wherein the fluidic channel comprises a nanochannel or a microchannel.

26. The method of claim 25, wherein applying a potential along the fluidic channel comprises generating an electrophoretic force therein.

27. The method of claim 25, wherein translocating the analyte comprises using a pressure differential.

28. The method of claim 25, wherein translocating the analyte comprises using a chemical gradient.

29. The method of claim 25, wherein preparing the analyte comprises hybridizing the biopolymer with a probe.

30. The method of claim 29, wherein a change in the electrical property corresponds to a location along the hybridized biopolymer containing the probe.

31. The method of claim 25, wherein the biopolymer comprises a double-stranded biopolymer target molecule.

32. The method of claim 31, further comprising preparing the analyte by contacting the target molecule with a first probe having a first probe specificity for recognition sites of the target molecule to form a first plurality of local ternary complexes, the first probe having a first predicted recognition site sequence.

33. The method of claim 32, further comprising using the electrical property to determine positional information of the first plurality of local ternary complexes.

34. The method of claim 33, wherein the positional information includes a parameter corresponding to a spatial distance between two local ternary complexes.

35. The method of claim 33, wherein preparing the analyte further comprises contacting the target molecule with a second probe having a second probe specificity for recognition sites of the target molecule to form a second plurality of local ternary complexes, the second probe having a second predicted recognition site sequence.

36. The method of claim 35, further comprising using the electrical property to determine positional information of the second plurality of local ternary complexes.

37. The method of claim 36, further comprising aligning positional information of at least the first and second plurality of local ternary complexes to determine a DNA sequence of the target.

38. The method of claim 25, wherein the biopolymer comprises a double-stranded nucleic acid target molecule having a plurality of binding sites disposed along the sequence thereof 39. The method of claim 38, wherein preparing the analyte comprises adding a plurality of probe molecules having a first sequence specificity to the double-stranded nucleic acid target molecule.

40. The method of claim 39, further comprising incubating the probe molecules having the first sequence specificity and the target molecule so as to effectuate preferential binding of the first probe molecules to both a first binding site and a second binding site of the target molecule.

41. The method of claim 40, further comprising using the voltage signal to measure a parameter related to a distance between the first binding site and the second binding site.

42. The method of claim 25, further comprising preparing the analyte by contacting the biopolymer with a first probe to create at least one probe-target complex at a recognition site of the biopolymer for which the first probe has a known specificity, while leaving uncomplexed, regions of the biopolymer for which the first probe is not specific.

43. The method of claim 42, wherein preparing the analyte further comprises contacting the biopolymer with a second probe to create at least one probe-target complex at a recognition site of the biopolymer for which the second probe has a known specificity, while leaving uncomplexed, regions of the target for which the second probe is not specific.

44. The method of claim 43, further comprising using the electrical property to detect and record complexed and uncomplexed regions of the biopolymer to create a first probe map of the first probe and a second probe map of the second probe, the first probe map and the second probe map incorporating information on the relative position of the hybridization of the probes.

45. The method of claim 44, further comprising determining a candidate sequence by ordering at least two probe sequences using positional information or a combination of overlapping sequences of the probe molecules and positional information.

46. The method of claim 44, wherein the first and second probe maps further incorporate information on an error of the positional information for each probe.

47. The method of claim 46, further comprising determining a candidate sequence by ordering at least two probe sequences using positional information and parameters relating to the error in positional information or a combination of overlapping sequences of the probe molecules and positional information and error in positional information.

48. A device for sensing electrical properties of analytes, the device comprising:
    a fluidic channel defined by a trench in a substrate;
    a pair of sensing electrodes disposed in the channel for sensing an electrical property therein, the pair of sensing electrodes comprising a first and a second sensing electrode disposed at two discrete laterally offset locations along a length of the fluidic channel, the pair of sensing electrodes being connected to a voltmeter for measuring the electrical property sensed by the pair of sensing electrodes and the pair of sensing electrodes not being connected to a voltage source; and
    a pair of electromotive electrodes disposed at a first end and a second end of the fluidic channel for applying a potential along the fluidic channel,
    wherein the fluidic channel comprises a nanochannel or a microchannel.

49. The device of claim 48, wherein the first sensing electrode is disposed on a first side of the fluidic channel and the second sensing electrode is disposed on an opposing side of the fluidic channel.

50. The device of claim 48, wherein each of the first and second sensing electrodes is disposed on a first side of the fluidic channel.

51. The device of claim 48, wherein each of the first and second sensing electrodes transverses the fluidic channel.

52. The device of claim 48, further comprising a plurality of fluidic channels.

53. The device of claim 48, further comprising a voltage amplifier disposed on the substrate.

54. The device of claim 48, wherein the fluidic channel has a width selected from a range of 1 nm to 5 μm.

55. The device of claim 48, wherein the fluidic channel has a depth selected from a range of 1 nm to 5 μm.

56. The device of claim 48, wherein the fluidic channel has a length selected from a range of 1 μm to 10 cm.

* * * * *